United States Patent [19]

Fevig et al.

[11] Patent Number: 5,462,964
[45] Date of Patent: Oct. 31, 1995

[54] DIPEPTIDE BORONIC ACID INHIBITORS OF TRYPSIN-LIKE ENZYMES

[75] Inventors: John M. Fevig, Lincoln University, Pa.; Matthew M. Abelman, Solana Beach, Calif.; Eugene C. Amparo, West Chester, Pa.; Joseph Cacciola; Charles A. Kettner, both of Willmington, Del.; Gregory J. Pacofsky, Durham, N.C.; Chia-Lin Wang, Taipei, Taiwan

[73] Assignee: The Du Pont Merck Pharmaceutical Company, Wilmington, Del.

[21] Appl. No.: 139,444

[22] Filed: Oct. 20, 1993

[51] Int. Cl.$^6$ .......................... A61K 31/40; C07D 207/04
[52] U.S. Cl. .......................... 514/423; 514/422; 514/414; 514/387; 514/375; 514/343; 514/314; 514/213; 514/183; 548/405; 548/413; 548/110; 546/15; 540/452; 540/485; 540/487
[58] Field of Search .................. 548/405, 413, 548/110; 514/423, 422, 414, 375, 387, 314, 343, 183, 213; 546/15; 540/452, 485, 487

[56] References Cited

U.S. PATENT DOCUMENTS

| | | | |
|---|---|---|---|
| 4,428,874 | 1/1984 | Svendsen | 260/112.5 |
| 4,450,105 | 5/1994 | Nagasawa et al. | 260/112.5 |
| 4,499,082 | 2/1985 | Shenvi et al. | 514/2 |
| 4,537,773 | 8/1985 | Shenvi et al. | 514/63 |
| 5,232,920 | 8/1993 | Neustadt | 514/212 |
| 5,288,707 | 2/1994 | Metternich | 514/19 |

FOREIGN PATENT DOCUMENTS

| | | | |
|---|---|---|---|
| 471651A2 | 2/1992 | European Pat. Off. | 548/405 |
| 0479489A2 | 4/1992 | European Pat. Off. | 548/405 |
| WO92/07869 | 5/1992 | WIPO . | |

OTHER PUBLICATIONS

Balasubramanian, et al. J. Med. Chem. 36, 300 (1993), Active Site–Directed . . . Series.

*Primary Examiner*—Joseph K. McKane

[57] ABSTRACT

The present invention relates to the discovery of new C-terminal boronic acid dipeptide inhibitors of trypsin-like enzymes such as thrombin and pharmaceutical compositions thereof.

12 Claims, No Drawings

DIPEPTIDE BORONIC ACID INHIBITORS OF TRYPSIN-LIKE ENZYMES

FIELD OF THE INVENTION

The present invention relates to the discovery of new C-terminal boronic acid dipeptide inhibitors of trypsin-like enzymes such as thrombin and pharmaceutical compositions thereof.

BACKGROUND OF THE INVENTION

The activity of many biological systems is mediated by proteolytic enzymes which cleave precursor proteins at specific amino acid residues. One major type of these enzymes, the serine proteases, are so named because the initial step in their proteolysis reactions is the attack of the hydroxyl of an active site serine on the amide carbonyl at the scissile site of the protein. This results in a tetrahedral intermediate which subsequently breaks down into an acyl enzyme and the amino terminus of the cleaved sequence. Hydrolysis of the acyl enzyme releases the carboxyl terminus and the free enzyme. A subclass of the serine proteases is composed of the trypsin-like enzymes, which cleave proteins site-specifically such that the liberated carboxyl terminus is arginine or lysine.

A great deal of research has been directed at finding mechanism-based inhibitors of serine proteases. In general, this approach has involved finding small molecules or peptides that both fit into the active site and contain a functionality able to interact with the active site serine. Irreversible inhibitors would contain a functionality that forms a covalent bond with the serine residue. Of more therapeutic interest are reversible inhibitors, which would contain a functionality that interacts with the serine residue to form a transient species that mimics the tetrahedral intermediate formed during cleavage of the natural substrate.

Several researchers have experimented with boron-containing reversible inhibitors of serine proteases. The binding of boronic acids to serine proteases most likely involves initial attack of the serine hydroxyl onto boron to form a tetrahedral boron "ate" complex. This complex can serve as a mimic of the tetrahedral intermediate formed during hydrolysis of the natural substrate, as disclosed by Zhong et. al., *J. Am. Chem. Soc.* 113, 9429 (1991). For example, Koehler et al. in *Biochemistry* 10, 2477 (1971) reports that 2-phenylethane boronic acid inhibits chymotrypsin at millimolar levels. The synthesis of boronic acid analogs of N-acyl-α-amino acids has yielded more effective inhibitors. Matteson et al. *J. Am. Chem. Soc.* 103, 5241 (1981) described Ac-boroPhe-OH, (R)-1-acetamido-2-phenylethane boronic acid, which inhibits chymotrypsin with a $K_i$ of 4 μM. More recently, Shenvi, in U.S. Pat. No. 4,537,773 disclosed that boronic acid analogs of α-amino acids, containing a free amino group, were effective inhibitors of aminopeptidases. Shenvi, in U.S. Pat. No. 4,499,082, disclosed that peptides containing an α-aminoboronic acid with a neutral side chain were more effective inhibitors of serine proteases, exceeding inhibitors disclosed earlier by as much as three orders of magnitude in potency.

The trypsin-like protease thrombin is the final protease in both the intrinsic and extrinsic pathways of the blood coagulation cascade and thus is of crucial importance in the blood coagulation process. Thrombin is responsible for the cleavage of fibrinogen to fibrin, which is then cross-linked by factor XIIIa, thereby stabilizing a developing blood clot. In addition, thrombin activates platelets and also factors V and VIII, which potentiate its own production, as described in Hemker and Beguin, Jolles et. al. "Biology and Pathology of Platelet Vessel Wall Interactions," 1986, pp. 219–226; Crawford and Scrutton in: Bloom and Thomas "Haemostasis and Thrombosis," 1987 pp. 47–77. Inhibitors of thrombin are expected to be effective in the treatment of thrombosis, a condition in which unbalanced activity of the hemostatic mechanism leads to intravascular thrombus formation. Direct thrombin inhibitors are also expected to be devoid of the side effects of bleeding and high interpatient variability which are common with heparin and vitamin K antagonist therapy (Green et al. *Thromb. res.* 1985, 37, 145–153).

Several mechanism-based thrombin inhibitors have been disclosed, most notably those based on the D-Phe-Pro-Arg sequence. The chloromethyl ketone Ac-D-Phe-Pro-ArgCH$_2$Cl disclosed by Kettner and Shaw *Thromb. Res.* 14, 969 (1979) was found to be a potent and selective irreversible inhibitor of human thrombin. The corresponding aldehyde Ac-D-Phe-Pro-Arg-H, desclosed by Bajuez et. al. *Folia Haematol.* 109, s. 16 (1982) was shown to be a reversible inhibitor of thrombin with a Ki= 75 nM. This class of reversible thrombin inhibitors is also exemplified by the trifluoromethyl ketone D-Phe-Pro-ArgCF$_3$ disclosed by Kolb et. al., AU-B-52881/86.

This series of tripeptide thrombin inhibitors was expanded to include the boronic acid derivatives which are exemplified by Ac-D-Phe-Pro-boroArgOH in Kettner and Shenvi, European Patent Application EP 293 881. This compound has a $K_i$=0.041 nM and is highly effective in the inhibition of blood coagulation both in vitro and in vivo. Additional boronic acid inhibitors of thrombin have been disclosed: Elgendy et al., *Tetrahedron Lett.* 33, 4209 (1992) have described peptides containing α-aminoboronic acids with aliphatic neutral sidechains which are thrombin inhibitors.

There have been patent disclosures which describe alternatives to the D-Phe residue in the D-Phe-Pro-Arg amino acid sequence. Metternich, in European Patent Application EP 471 651, has described peptides containing boroArginine and boroLysine which contain at least one unnatural amino acid residue. Kakkar in PCT Application WO 92/07869 has claimed peptide thrombin inhibitors of the general structure, X-Aa$_1$-Aa$_2$-NH—CH(Y)-Z where Aa$_1$ and Aa$_2$ are unnatural amino acid residues, Z can be a variety of electrophilic groups including boronic acid, and Y can be a variety of basic sidechains. Tripeptide agents limited to α-alkyl and α-aryl or heteroaryl substituted glycines conjugated to -Pro-Arg-H have been disclosed by Lilly in European Patent Application EP 0 479 489 A2. Sandoz has disclosed in European Patent Application EP 471 651 A2 boroLysine and boroArginine peptide analogs containing at least one unnatural hydrophobic α-amino acid substituted with groups such as trimethylsilyl or naphthyl. Balasubramanian et. al., in *J. Med. Chem.* 36, 300 (1993), has reported replacements for the D-Phe of D-Phe-Pro-Arg-H and found the dihydrocinnamoyl group to be effective, although somewhat less potent.

Despite the foregoing, more efficacious and specific thrombin inhibitors are needed as potentially useful therapeutic agents for the treatment of thrombosis. The present invention relates to an extensive study of non-amino acid replacements for the D-Phe of the boropeptide D-Phe-Pro-boroArgOH.

SUMMARY OF THE INVENTION

[1] There is provided by this invention a compound of formula (I)

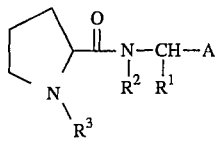
(I)

or a pharmaceutically acceptable salt, hydrate or prodrug thereof, wherein:

$R^1$ is
  a) —($C_1$-$C_{12}$ alkyl)-X, or
  b)
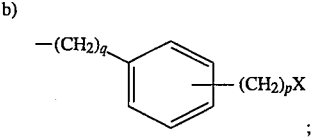
;

X is
  a) halogen
  b) —CN,
  c) —$NO_2$,
  d) —$CF_3$,
  e) —$NH_2$,
  f) —NHC(=NH)H,
  g) —NHC(=NH)NHOH,
  h) —NHC(=NH)NHCN,
  i) —NHC(=NH)$NHR^2$,
  j) —NHC(=NH)NHC(=O)$R^2$,
  k) —C(=NH)$NHR^2$,
  l) —C(=NH)NHC(=O)$R^2$,
  m) —C(=O)$NHR^2$,
  n) —$CO_2R^2$,
  o) —$OR^2$,
  p) —$OCF_3$,
  q) —$SR^2$, or
  q) —SC(=NH)$NHR^2$;

$R^2$ is
  a) hydrogen,
  b) $C_1$-$C_4$ alkyl,
  c) aryl,
  d) —($C_1$-$C_4$ alkyl)-aryl, where aryl is defined above;

$R^3$ is
  a) —C(=O)$CR^6R^7$-aryl,
  b) —C(=O)—($C_2$-$C_5$ alkenyl)-aryl,
  c) —C(=O)$CR^6R^7$$(CH_2)_r$—W—$(CR^6R^7)_r$-aryl,
  d) —C(=O)$CR^6R^7$$(CH_2)_r$$CR^8R^9$-aryl,
  e) —C(=O)$CR^6R^7$$(CH_2)_r$$CR^8R^9$-heteroaryl, ,
  f) —C(=O)$CR^6R^7$$(CH_2)_r$$CR^8R^9$-heterocycle,
  g) —C(=O)-aryl, wherein aryl is defined as above,
  h) —C(=O)-heteroaryl,
  i) —C(=O)-heterocycle,
  j) —C(=O)O$(CH_2)_r$-adamantyl,
  k) —C(=O)$(CH_2)_r$—($C_5$-$C_7$ cycloalkyl),
  l) —C(=O)$(CH_2)_r$—W—($C_5$-$C_7$ cycloalkyl), m)
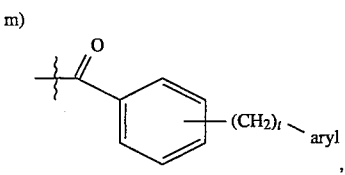

wherein aryl is limited to phenyl, n)
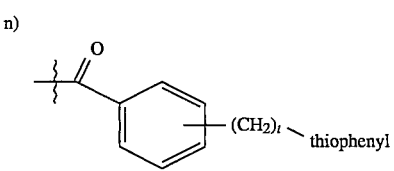

o)
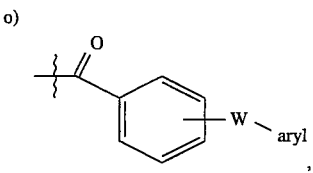

wherein aryl is limited to phenyl, p)
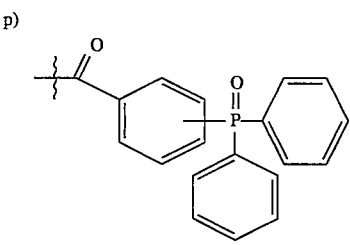

q)
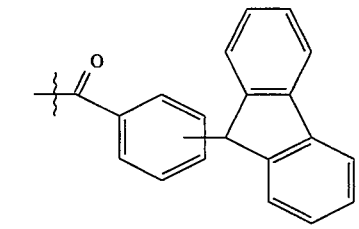

r)
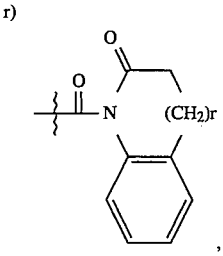

-continued
s) 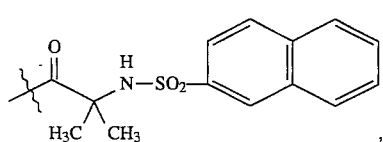
t) 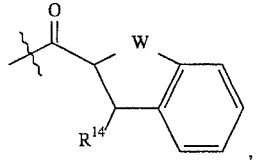
u) 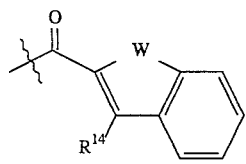
v) 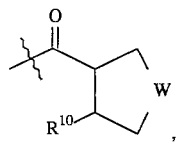
w) 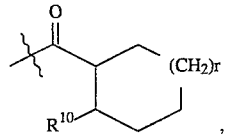
x) 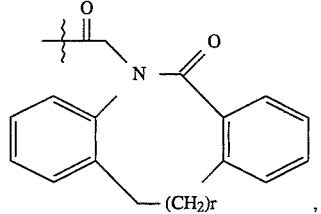
y) 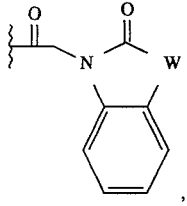
-continued
z) 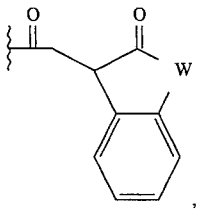
aa) 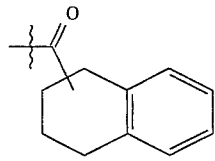
bb) 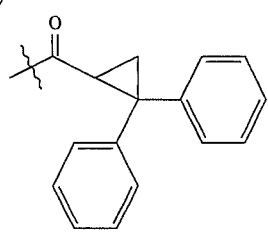
cc) 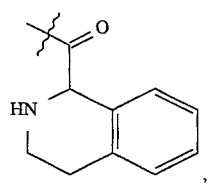
dd) 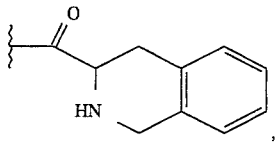
ee) 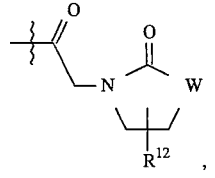
ff) 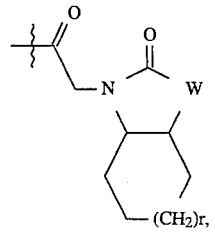
or gg)

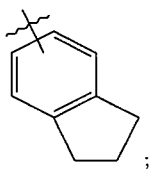

$R^4$ and $R^5$ are independently selected at each occurrence from the group consisting of:
a) hydrogen,
b) $C_1$–$C_4$ alkyl,
c) —($C_1$–$C_4$ alkyl)-aryl, or
d) —$C_5$–$C_7$ cycloalkyl;

$R^6$, $R^7$, $R^8$ and $R^9$ are independently selected at each occurrence from the group consisting of:
a) hydrogen,
b) $C_1$–$C_4$ alkyl,
c) $C_1$–$C_4$ alkoxy,
d) aryl,
e) —($C_1$–$C_4$ alkyl)-aryl,
f) —O-aryl, or
g) —$(CH_2)_p$—$CO_2R^4$;

$R^{10}$ is phenyl, where phenyl is optionally substituted with one to three substituents selected from the group consisting of: halogen, $C_1$–$C_4$ alkyl, $C_1$–$C_4$ alkoxy, methylenedioxy, —$NO_2$, —$CF_3$, $OCF_3$, —$S(O)_r$—(C1-C4-alkyl), —OH, —$NH_2$, —NH($C_1$–$C_4$ alkyl), —N($C_1$–$C_4$ alkyl)$_2$, —NHC(=O)$R^4$, $NHCO_2R^4$, —$(CH_2)_p$—$CO_2R^4$;

$R^{12}$ is:
a) hydrogen,
b) $C_1$–$C_4$ alkyl,
c) aryl,
c) —($C_1$–$C_4$ alkyl)-aryl, or
d) $C_5$–$C_7$ cycloalkyl;

A is
a) —$BY^1Y^2$,
b) —C(=O)$CF_3$,
c) —$PO_3H_2$, or
d) —$CO_2H$;

W is
a) —O—,
b) —$S(O)_r$—,
c) —$NR^4$—,
d) —NC(=O)$R^4$—, or
e) —$NCO_2R^4$—;

$Y^1$ and $Y^2$ are
a) —OH,
b) —F,
c) —$NR^4R^5$,
d) $C_1$–$C_8$ alkoxy, or when taken together $Y^1$ and $Y^2$ form a
e) cyclic boron ester where said chain or ring contains from 2 to 20 carbon atoms and, optionally, 1–3 heteroatoms which can be N, S, or O,
f) cyclic boron amide where said chain or ring contains from 2 to 20 carbon atoms and, optionally, 1–3 heteroatoms which can be N, S, or O,
g) cyclic boron amide-ester where said chain or ring contains from 2 to 20 carbon atoms and, optionally, 1–3 heteroatoms which can be N, S, or O;

n is independently selected at each occurrence from 0 or 1;

p is independently selected at each occurrence from 0 to 3;

q is independently selected at each occurrence from 0 to 4;

r is independently selected at each occurrence from 0 to 2;

t is independently selected at each occurrence from 1 to 3.

[2] Preferred compounds of formula (I) are those compounds wherein:

$R^1$ is
a) —$(CH_2)_4NHR^2$,
b) —$(CH_2)_3NHC(=NH)NHR^2$,
c) —$(CH_2)_3NHC(=NH)H$,
d) —$(CH_2)_3SC(=NH)NHR^2$;

$R^2$ is hydrogen or $C_1$–$C_4$ alkyl;

$R^3$ is
a) —$COCR^6R^7$-aryl,
b) —$COCR^6R^7(CH_2)_r$—W—$(CR^6R^7)_r$-aryl,
c) —$COCR^6R^7(CH_2)_rCR^8R^9$-aryl,
d) —$COCR^6R^7(CH_2)_rCR^8R^9$-heteroaryl, e)

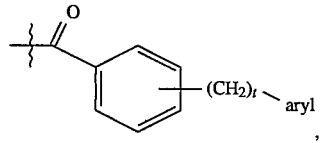

wherein aryl is limited to phenyl, f)

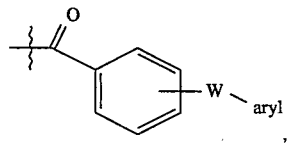

wherein aryl is limited to phenyl, g)

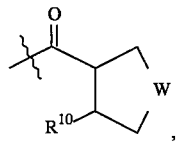

or h)

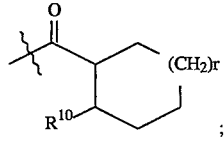

$R^4$ is independently selected at each occurrence from the group consisting of:
a) hydrogen,
b) $C_1$–$C_4$ alkyl,
c) —($C_1$–$C_4$ alkyl)-aryl;

$R^6$, $R^7$, $R^8$, and $R^9$ are independently selected at each occurrence from the group consisting of:
a) hydrogen, or
b) $C_1$–$C_4$ alkyl;

$R^{10}$ is phenyl, where phenyl is optionally substituted with one to three substituents selected from the group consisting of: halogen, $C_1$–$C_4$ alkyl, $C_1$–$C_4$ alkoxy, —$CF_3$;

A is
a) —$BY^1Y^2$;

W is
a) —O—,
b) —S(O)$_r$—,
c) —$NR^4$—,
d) —NC(=O)$R^4$—, or
e) —$NCO_2R^4$—;

$Y^1$ and $Y^2$ are
a) —OH,
b) $C_1$–$C_8$ alkoxy, or when taken together $Y^1$ and $Y^2$ form a
c) cyclic boron ester where said chain or ring contains from 2 to 20 carbon atoms and, optionally, 1–3 heteroatoms which can be N, S, or O;

r is independently selected at each occurrence from 0 to 2;

t is 1.

More preferred compounds of formula (I) are those compounds wherein:

$R^1$ is
a) —$(CH_2)_4NH_2$,
b) —$(CH_2)_3NHC(NH)NH_2$,
c) —$(CH_2)_3NHC(NH)H$,
d) —$(CH_2)_3SC(NH)NH_2$
e) —$(CH_2)_3NHC(NH)NHCH_3$;

$R^2$ is hydrogen $R^3$ is
a) —$COCR^6R^7(CH_2)_r$—W—$(CR^6R^7)_t$-aryl,
b) —$COCR^6R^7(CH_2)_tCR^8R^9$-aryl, c)
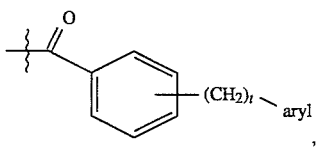

d)
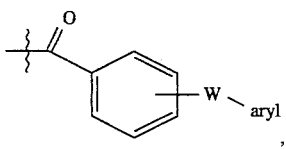

e)
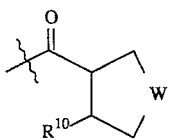

or f)
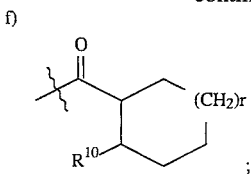

$R^4$ is independently selected at each occurrence from the group consisting of:
a) hydrogen,
b) $C_1$–$C_4$ alkyl,
c) —$(C_1$–$C_4$ alkyl)-aryl;

$R^6$, $R^7$, $R^8$, and $R^9$ are independently at each occurrence from the group consisting of:
a) hydrogen, or
b) $C_1$–$C_4$ alkyl;

$R^{10}$ is phenyl, where phenyl is optionally substituted with one to three substituents selected from the group consisting of: halogen, $C_1$–$C_4$ alkyl, $C_1$–$C_4$ alkoxy, methylenedioxy, —$NO_2$, —$CF_3$, —S(O)$_r$—($C_1$–$C_4$ alkyl), —OH, —$NH_2$, —NH($C_1$–$C_4$ alkyl), —N($C_1$–$C_4$ alkyl)$_2$, —NHC(=O)$R^4$, $NHCO_2R^4$—$(CH_2)_p$—$CO_2R^4$;

A is
a) —$BY^1Y^2$;

W is
a) —O—,
b) —S(O)$_r$—,
c) —$NR^4$—,
d) —NC(=O)$R^4$—, or
e) —$NCO_2R^4$—;

$Y^1$ and $Y^2$ are
a) —OH,
b) $C_1$–$C_8$ alkoxy, or when taken together $Y^1$ and $Y^2$ form a
c) cyclic boron ester where said chain or ring contains from 2 to 20 carbon atoms and, optionally, 1–3 heteroatoms which can be N, S, or O;

p is 0–4 independently selected at each occurrence from 0 to 2;

t is 1.

Illustrative of the preferred compounds of this invention are the following:

(a) $PhCH_2CH_2C(=O)$-Pro-NHCH[$(CH_2)_3NHC(=NH)NH_2$]$BO_2C_{10}H_{16}$
(b) $PhCH_2CH_2C(=O)$-Pro-NHCH[$(CH_2)_4NH_2$]$B(OH)_2$
(c) $PhOCH_2C(=O)$-Pro-NHCH[$(CH_2)_4NH_2$]$B(OH)_2$
(d) $PhOC(CH_3)_2C(=O)$-Pro-NHCH[$(CH_2)_4NH_2$]$B(OH)_2$
(e) $PhSCH_2C(=O)$-Pro-NHCH[$(CH_2)_4NH_2$]$B(OH)_2$
(f) 3-$CH_3C_6H_4CH_2CH_2$ C(=O)-Pro-NHCH[$(CH_2)_4NH_2$]$BO_2C_{10}H16$
(g) 2-$CF_3C_6H_4CH_2CH_2$ C(=O)-Pro-NHCH[$(CH_2)_4NH_2$]$BO_2C_{10}H16$
(h) (4-$CH_3O$-3-$CH_3$)-$C_6H_3CH_2CH_2$ C(=O)-Pro-NHCH[$(CH_2)_4NH_2$]$BO_2C_{10}H_{16}$
(i) 3-[(2-$CF_3)C_6H_4CH_2]C_6H_4$ C(=O)-Pro-NHCH[$(CH_2)_4NH_2$]$BO_2C_{10}H_{16}$
(j) 3-(PhS)$C_6H_4$C(=O)-Pro-NHCH[$(CH_2)_4NH_2$]$BO_2C_{10}H_{16}$
(k) 3-(PhO)$C_6H_4$C(=O)-Pro-NHCH[$(CH_2)_4NH_2$]$BO_2C_{10}H_{16}$
(l) trans-[4-(3-$CF_3C_6H_4$)-Pyrrolidine-3 -(C=O)]Pro-

NHCH[(CH$_2$)$_4$NH$_2$]BO$_2$C$_{10}$H$_{16}$ (m) [(1R,2R)-2-Phenylcyclohexanecarbonyl] Pro-NHCH[(CH$_2$)$_4$NH$_2$]B(OH)$_2$ (n) 2-(C$_5$H$_4$N)CH$_2$CH$_2$ C(=O)-Pro-NHCH[(CH$_2$)$_4$NH$_2$]BO$_2$C$_{10}$H$_{16}$ (o) 2-(Ph)-C$_6$H$_4$CH$_2$CH$_2$ C(=O)-Pro-NHCH[(CH$_2$)$_4$NH$_2$]BO$_2$C$_{10}$H$_{16}$ (p) 3,4-(Cl)$_2$-C$_6$H$_3$CH$_2$ C(=O)-Pro-NHCH[(CH$_2$)$_3$NHC(=NH)NH$_2$]BO$_2$C$_{10}$H$_{16}$ (q) PhCH$_2$CH$_2$C(=O)-Pro-NHCH[(CH$_2$)$_3$NHC(=NH)H]B(OH)$_2$.

DETAIL DESCRIPTION OF THE INVENTION

As used throughout the specifications, the following abbreviations for amino acid residues or amino acids apply:
Ala=L-alanine
Arg=L-arginine
Asn=L-asparagine
Asp=L-aspartic acid
Cys=L-cysteine
Gln=L-glutamine
Glu=L-glutamic acid
Gly=glycine
His=L-histidine
Ile=L-isoleucine
Leu=L-leucine
Lys=L-lysine
Met=L-methionine
Phe=L-phenylalanine
Pro=L-proline
Ser=L-serine
Thr=L-threonine
Trp=L-tryptophan
Tyr=L-tyrosine
Val=L-valine
Sar=or N-methylglycome The "D" prefix for the foregoing abbreviations indicates the amino acid is in the D-configuration. "D,L" indicates the amino is present in mixture of the D- and the L-configuration. The prefix "boro" indicates amino acid residues where the carboxyl is replaced by a boronic acid or a boronic acid ester. For example, if R$^1$ is isopropyl and Y$^1$ and Y$^2$ are OH, the C-terminal residue is abbreviated "boroVal-OH" where "—OH" indicates the boronic acid is in the form of the free acid. The pinanediol boronic acid ester is abbreviated "—C$_{10}$H$_{16}$". Thus, an example of the chemical structure based on the nomenclature used herein is:

represents

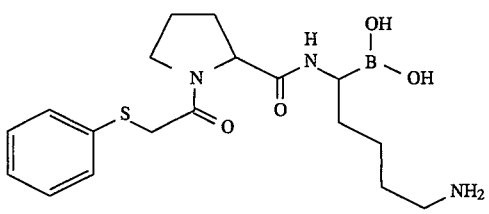

Examples of other useful diols for esterification with the boronic acids are 1,2-ethanediol, 1,3-propanediol, 1,2-propanediol, 2,3-butanediol, 1,2-diisopropylethanediol, 5,6-decanediol, and 1,2-dicyclohexylethanediol. Other common abbreviations are: THF, tetrahydrofuran; Et$_3$N, triethylamine; NaHCO$_3$, sodium bicarbonate; EtOAc, ethyl acetate; Na$_2$SO$_4$, sodium sulfate; h, hours; min, minutes; MeOH, methanol; HCl, hydrochloric acid; DMF, N,N-dimethylformamide; Et$_2$O, diethyl ether; NH$_4$Cl, ammonium chloride; CBZ, benzyloxycarbonyl; BSA, benzenesulfonic acid; THF, tetrahydrofuran; Boc-, t-butoxycarbonyl-; Ac-, acetyl; pNA, p-nitro-aniline; DMAP, 4-N,N-dimethylaminopyridine; Tris, Tris(hydroxymethyl)aminomethane; MS, mass spectrometry; FAB/MS, fast atom bombardment mass spectrometry. LRMS(NH$_3$—CI) and HRMS(NH$_3$—CI) are low and high resolution mass spectrometry, respectively, using NH$_3$ as an ion source.

The term "amine-blocking group" or "amine-protecting group" as used herein, refers to various acyl, thioacyl, alkyl, sulfonyl, phosphoryl, and phosphinyl groups comprised of 1 to 20 carbon atoms. Substitutents on these groups maybe either alkyl, aryl, alkaryl which may contain the heteroatoms, O, S, and N as a substituent or as an in chain component. A number of amine-blocking groups are recognized by those skilled in the art of organic synthesis. Examples of suitable groups include formyl, acetyl, benzoyl, trifluoroacetyl, and methoxysuccinyl; aromatic urethane protecting groups, such as, benzyloxycarbonyl; and aliphatic urethane protecting groups, such as t-butoxycarbonyl or adamantyloxycarbonyl. Gross and Meienhofer, eds., *The Peptides*, Vol 3; 3–88 (1981), Academic Press, New York, and Greene and Wuts *Protective Groups in Organic Synthesis*, 315–405 (1991), J. Wiley and Sons, Inc., New York disclose numerous suitable amine protecting groups and they are incorporated herein by reference for that purpose.

"Amino acid residues" as used herein, refers to natural or unnatural amino acids of either D- or L-configuration. Natural amino acids residues are Ala, Arg, Asn, Asp, Cys, Gln, Glu, Gly, His Ile, Leu, Lys, Met, Phe, Pro, Ser, Thr, Trp, Tyr, and Val. Roberts and Vellaccio, *The Peptides*, Vol 5; 341–449 (1983), Academic Press, New York, discloses numerous suitable unnatural amino acids and is incorporated herein by reference for that purpose.

"Amino acids residues" also refers to various amino acids where sidechain functional groups are coupled with appropriate protecting groups known to those skilled in the art. *"The Peptides"*, Vol 3, 3–88 (1981) discloses numerous suitable protecting groups and is incorporated herein by reference for that purpose.

As used herein, "alkyl" is intended to include both branched and straight-chain saturated aliphatic hydrocarbon groups having the specified number of carbon atoms; "alkoxy" represents an alkyl group of indicated number of carbon atoms attached through an oxygen bridge; "cycloalkyl" is intended to include saturated ring groups, including mono-, bi- or poly-cyclic ring systems, such as cyclopropyl, cyclobutyl, cyclopentyl, cyclohexyl, cycloheptyl, adamantyl and cyclooctyl, and so forth. "Alkenyl" is intended to include hydrocarbon chains of either a straight or branched configuration and one or more unsaturated carbon-carbon bonds which may occur in any stable point along the chain, such as ethenyl, propenyl, and the like. "Halo" or "halogen" as used herein refers to fluoro, chloro, bromo, and iodo.

As used herein, "aryl" or is intended to mean phenyl, naphthyl, biphenyl or fluorenyl which may be unsubstituted or include optional substitution with one to five substituents.

The term "heteroaryl" is meant to include 5-, 6- or 10-membered mono- or bicyclic aromatic rings, which can optionally contain from 1 to 3 heteroatoms selected from the group consisting of O, N, and S; said ring(s) may be unsubstituted or include optional substitution with one to three substituents. Included in the definition of the group heteroaryl, but not limited to, are the following: 2-, or 3-, or 4-pyridyl, 2- or 3-furyl, thiophenyl, 2-, or 4-, or 5-imidazoyl, 2-, or 4-, or 5-oxazoyl, 2-, or 4-, or 5-thiazoyl, 2- or 3-benzofuranyl, 2- or 3-benzo[b]thiophenyl, 2-, or 3-, or 4-quinolinyl; 1-, or 3-, or 4-isoquinolinyl; 2- or 3-pyrrolyl; 1- or 2-benzimidazoyl, 2-benzoxazoyl, 1- or 2-benzothiazoyl, indolinoyl-2-onyl, indolinoyl, indolyl, pyrrolyl, 2- or 4- or 5-thiazolyl; 2-benzothiazolyl; 3- or 4- or 5-isoxazolyl; 3- or 4- or 5-pyrazolyl; 3- or 4- or 5-isothiazolyl; 3- or 4-pyridazinyl; 2- or 4- or 5-pyrimidinyl; 2-pyrazinyl; 2-triazinyl; 3- or 4-cinnolinyl; 1-phthalazinyl; 2- or 4-quinazolinyl; or 2-quinoxalinyl ring. Particularly preferred are 2-, 3-, or 4-pyridyl; 2-, or 3-furyl; 2-, or 3-thiophenyl; 2-, 3-, or 4-quinolinyl; or 1-, 3-, or 4-isoquinolinyl.

The term "heterocycle" is meant to include 5-, 6- or 10-membered mono- or bicyclic rings, which can optionally contain from 1 to 3 heteroatoms selected from the group consisting of O, N, and S; said ring(s) may be unsubstituted or include optional substitution with one to three substituents. Included in the definition of the group heterocycle, but not limited to, are tetrahydroisoquinolinyl, tetrahydroquinolinyl, tetrahydrofuranyl, tetrahydrothiophenyl, piperidinyl, piperazinyl, morpholinyl. Particularly preferred are 1-, 3-, or 4-tetrahdroisoquinolinyl.

The substituents that may be attached to the aryl, heteroaryl or heterocycle ring(s) may be independently selected at each occurrence from the group consisting of: halogen, $C_1$–$C_4$ alkyl, $C_1$–$C_4$ alkoxy, methylenedioxy, —$NO_2$, —$OCF_3$, —$CF_3$, —SH, —S(O)$_r$—($C_1$–$C_4$ alkyl), —CN, —OH, —$NH_2$, —NH($C_1$–$C_4$ alkyl), —N($C_1$–$C_4$ alkyl)$_2$, —NHC(=O)$R^4$, —($CH_2$)$_p$—$CO_2R^4$, or phenyl which may be unsubstituted or substituted with $R^{13}$.

It is understood that many of the compounds of the present invention contain one or more chiral centers and that these stereoisomers may possess distinct physical and biological properties. The present invention comprises all of the stereoisomers or mixtures thereof. If the pure enantiomers or diasteromers are desired, they may be prepared using starting materials with the appropriate stereochemistry, or may be separated from mixtures of undesired stereoisomers by standard techniques, including chiral chromatography and recrystallization of diastereomeric salts.

By "stable compound" or "stable structure" is meant herein a compound that is sufficiently robust to survive isolation to a useful degree of purity from a reaction mixture, and formulation into an efficacious therapeutic agent.

As used herein, "pharmaceutically acceptable salts" refer to derivatives of the disclosed compounds wherein the parent compound of formula (I) is modified by making acid or base salts of the compound of formula (I). Examples of pharmaceutically acceptable salts include, but are not limited to, mineral or organic acid salts of basic residues such as amines; alkali or organic salts of acidic residues such as carboxylic acids; and the like.

"Prodrugs" are considered to be any covalently bonded carriers which release the active parent drug according to formula (I) in vivo when such prodrug is administered to a mammalian subject. Prodrugs of the compounds of formula (I) are prepared by modifying functional groups present in the compounds in such a way that the modifications are cleaved, either in routine manipulation or in vivo, to the parent compounds. Prodrugs include compounds of formula (I) wherein hydroxy, amine, or sulfhydryl groups are bonded to any group that, when administered to a mammalian subject, cleaves to form a free hydroxyl, amino, or sulfhydryl group, respectively. Examples of prodrugs include, but are not limited to, acetate, formate and benzoate derivatives of alcohol and amine functional groups in the compounds of formula (I); and the like.

Pharmaceutically acceptable salts of the compounds of the invention can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences,* 17th ed., Mack Publishing Company, Easton, Pa., 1985, p. 1418, the disclosure of which is hereby incorporated by reference.

Synthesis

The compounds of formula (I) were or can be prepared by the general procedures described in the following schemes. It will be understood by those skilled in the art of organic synthesis that the particular process or reagents chosen for a chemical transformation should be consistent with the functionality present on the molecules involved and this will sometimes require judgement as to the order and manner in which the desired synthetic sequence is performed. Other procedures for synthesis of the compounds of the present invention can be found in Kettner and Shenvi, U.S. Pat. No. 5,187,157, as well as Applicant's Assignee's commonly assigned patent applications U.S. Ser. No. 08/010,731 (filed Jan. 29, 1993), U.S. Ser. No. 08/036,378 (filed Mar. 24, 1993), and U.S. Ser. No. 08/052,835 (filed Apr. 27, 1993); all of which are hereby incorporated by reference.

Scheme 1 outlines the general procedure employed when $R^3$ in dipeptides of Formula (I) is an acyl group and the C-terminus is a boronic acid derivative of lysine, arginine or the isothiouronium derivative thereof. There are many synthetic methods for preparing amides (III) beginning with L-proline ester hydrochlorides, of which three methods are preferred. In the first method, a 0° C. solution of the proline ester in a suitable solvent, such as but not limited to tetrahydrofuran or dichloromethane, is treated with one equivalent of the desired acid chloride (IIa) and two equivalents of tertiary amine base, preferably triethylamine. The mixture is allowed to warm to room temperature and stirred for several hours. Standard aqueous workup provides the desired amide (III). This method is generally preferred when $R^3$ is such that the acid chloride is commercially available.

The second method is the mixed anhydride procedure of Anderson, et. al. described in *J. Am. Chem. Soc.* 89, 5012 (1967). In this method, a 0° C. solution of the carboxylic acid (IIb) in non-protic solvent, such as tetrahydrofuran, is treated with one equivalent of tertiary amine base, preferably N-methylmorpholine and one equivalent of isobutyl chloroformate. After 15 minutes, the resulting isobutyl mixed anhydride is treated sequentially with the amine salt and one equivalent of triethylamine or N-methylmorpholine. The resulting mixture is typically allowed to warm to room temperature, stirred for one to several hours and then subjected to standard aqueous workup.

Scheme 1

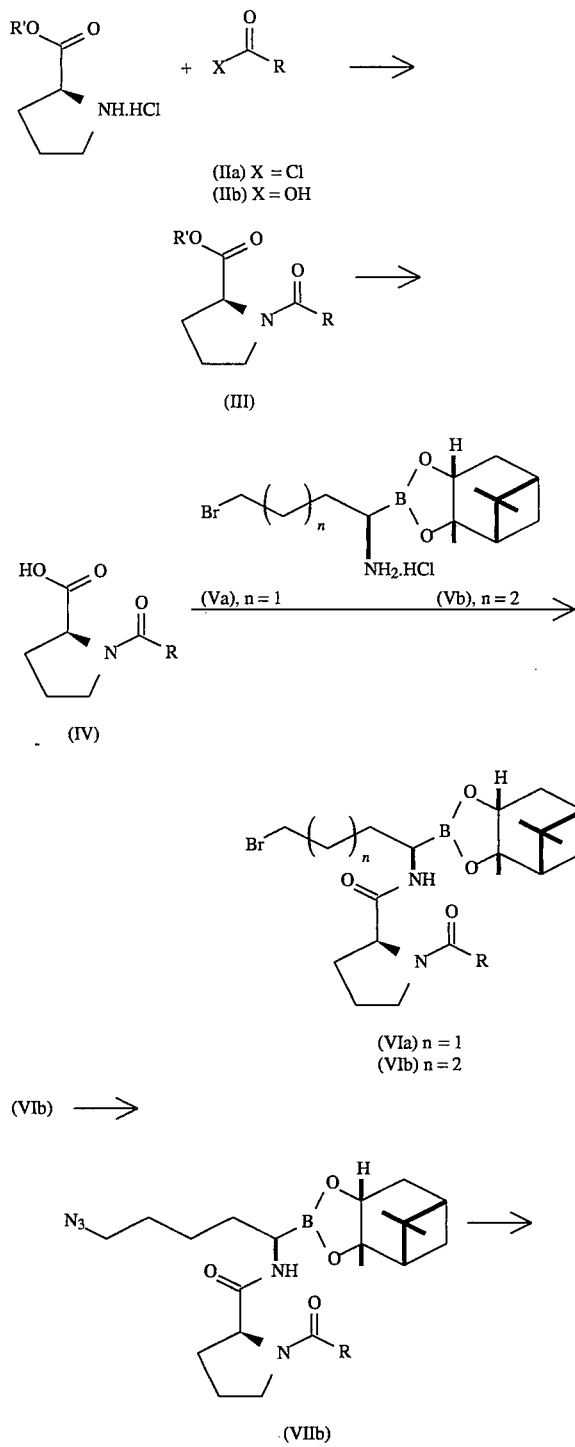

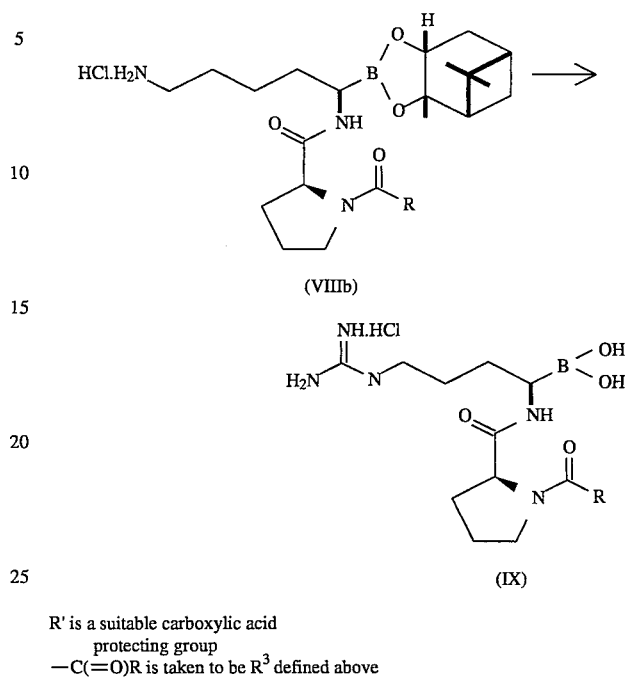

R' is a suitable carboxylic acid protecting group
—C(=O)R is taken to be $R^3$ defined above The third method is the dicyclohexylcarbodiimide/ 1-hydroxybenzotriazole (DCC/HOBT) method of Konig and Geiger, *Chem. Ber.* 103, 788 (1970). In this method, a solution of amine salt and carboxylic acid (IIb) in N,N-dimethylformamide or tetrahydrofuran can be treated with one equivalent of DCC, HOBT and triethylamine. The resulting mixture can be stirred for several hours or overnight and subjected to standard aqueous workup.

The standard aqueous workup referred to above typically involves removing the solvent in vacuo and then diluting the residue with a solvent such as ethyl acetate. This solution can be then washed sequentially with dilute aqueous acid, saturated aqueous sodium bicarbonate and brine. After drying over magnesium sulfate or sodium sulfate, the solution is concentrated in vacuo to afford the crude amide (III). In many cases this material is sufficiently pure to make unnecessary further purification. If purification of (III) is necessary, it is generally best done by flash column chromatography on silica gel.

The choice of ester protecting group R' on the amine salt depends upon the functionality present in —C(=O)R (identical to $R^3$ group defined above) and is generally methyl, benzyl or tert-butyl. Those skilled in the art of organic synthesis will be able to determine which ester is appropriate considering the functionality in $R^3$ and determine an appropriate method for cleavage to the carboxylic acid (IV).

The synthesis of the aminoboronates (Va) and (Vb) and their subsequent coupling with the carboxylic acid (IV) to give the bromides (VIa) and (VIb) was performed using the procedures described by Kettner and Shenvi U.S. Pat. No. 5,187,157.

The preferred method for preparing the borolysine analogs (VIIIb) and (IX) involves an azide displacement of the bromide (VIb) with sodium azide in DMF at 100° C. to give (VIIb). This azide can be reduced according any of the various methods for reduction of the azide to the corresponding amine found in Hudlicky, *Reductions In Organic Synthesis,* John Wiley and Sons, pp. 134 (1984). A preferred method involves hydrogenation over Pearlman's catalyst (palladium hydroxide on carbon) to afford the borolysine ester (VIIIb). Removal of the pinanediol ester is best accomplished by a transesterification reaction using excess phenylboronic acid. This procedure gives the free boronic acid (IX) which can be further purified by ion exchange chromatography.

Scheme 2 outlines the procedures employed for converting the bromide (VIa) to the boroarginine analog and to the isothiouronium, N-methylarginine and formamidino derivatives thereof. The bromide (VIa) was taken on to the corresponding isothiouronium analog (X) by treating with thiourea as described by Kettner and Shenvi in U.S. Pat. No. 5,187,157.

The preferred method for preparing the boroarginine analogs (XIa) and (XIIIa) involves the formamidation of the boroornithine derivative (VIIIa), derived from (VIa) as described for the borolysine analog, with aminoiminomethanesulfonic acid and 4-dimethylaminopyridine (Kim et al. *Tetrahedron Lett.* 29, 3183 (1988). This affords guanidine (XIa) which can be transesterified to the free boronic acid (XIIIa). Treatment of the boroornithine derivative (VIIIa) with N-methylaminoiminomethanesulfonic acid reported in Walter et. al. *Liebigs Ann. Chem.* 722, 98 (1969) under the same reaction conditions affords the N-methylguanidine (XIb) which can be similarly transesterified to the free boronic acid (XIIIb).

The formamidino analog (XII) can also be prepared from the boroornithine (VIIIa) by treatment with ethyl formimidate. Transesterification with phenylboric acid then provides the boronic acid (XIIa).

Scheme 2

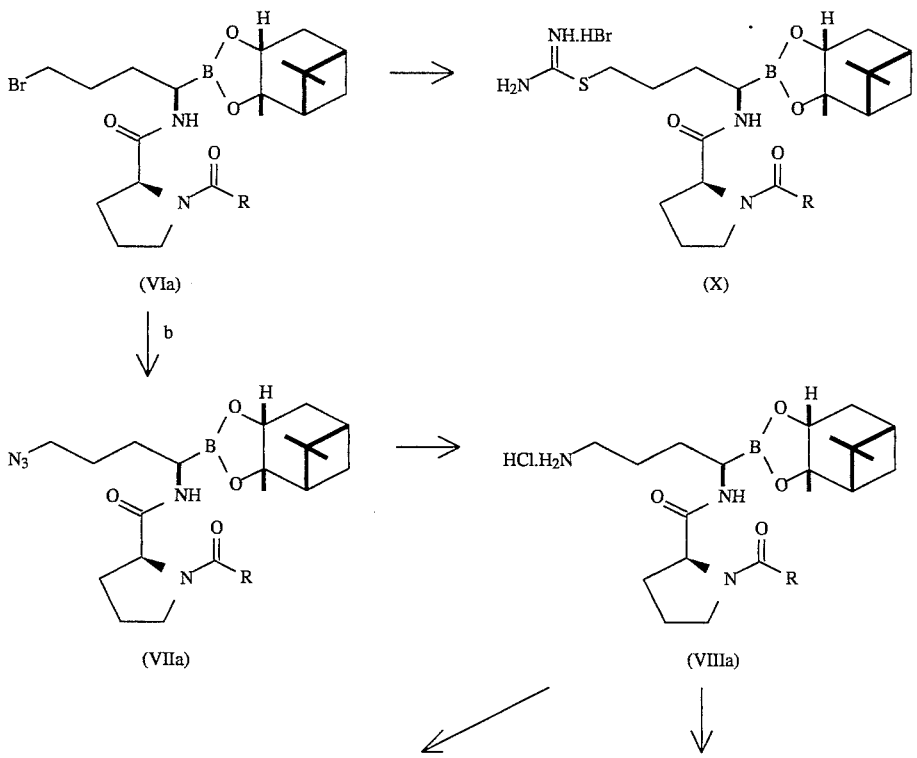

Scheme 2

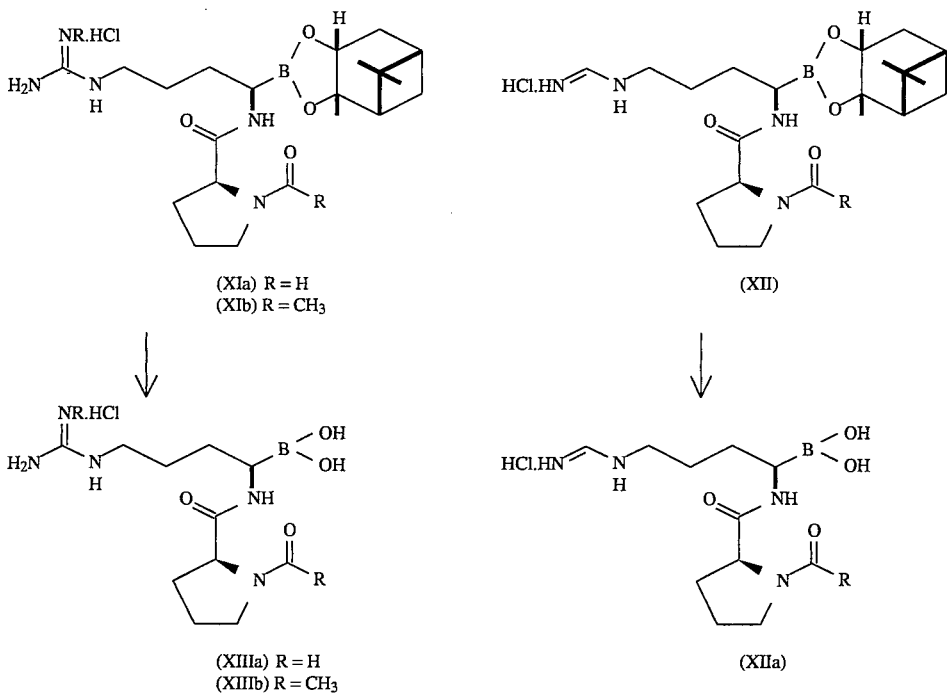

(XIa) R = H
(XIb) R = CH₃

(XIIIa) R = H
(XIIIb) R = CH₃

(XII)

(XIIa)

For many of the inhibitors contained in this invention, the required acid chloride (IIa) or carboxylic acid (IIb) are commercially available, in which case the synthesis followed the steps outlined in Schemes 1 & 2. When (IIa) or (IIb) were not commercially available, they were synthesized by the general routes outlined in Schemes 3–12 or by other standard techniques familiar to those skilled in the art of organic synthesis. Subsequently, they can be coupled with a proline ester and elaborated to the desired boronic acid inhibitors following the procedures outlined in Schemes 1 and 2.

The substituted hydrocinnamic acids (Table 1), wherein the aryl in $R^3$ is substituted, can be prepared by the general route shown in Scheme 3. Wittig olefination, using known reagents of general formula Ph₃P=CHCO₂R', of the appropriately substituted aldehyde or ketone (XIV) gives the ester (XV). Various conditions for reduction of the double bond are reported in Hudlicky (1984), however a preferred method was hydrogenation using palladium on carbon catalyst. Cleavage of the acid protecting group can be affected by a variety of conditions depending on the choice of R'. In the case of a benzyl ester (where R'=—CH₂C₆H₅), hydrogenolysis of an alcohol solution of the compound may be effected under an atmosphere of hydrogen gas in the presence of platinum or palladium on carbon catalyst according to the reported by Harthey and Simonoff, *Org. React.* VII, 263 (1953). In the case with a methyl ester (where R'=—CH₃), treatment of an ethanol solution of the compound with an aqueous base, such as one equivalent of sodium hydroxide solution, will give the desired acid. In the case of the t-butyl ester (where R'=—C(CH₃)₃), cleavage by acid under anhydrous conditions; for example trifluoroacetic acid in dichloromethane solution removes the t-butyl ester at ambient temperature as reported by Bryan et. al., *J. Am. Chem. Soc.* 99, 2353 (1977). A number of alternative esters and procedures are detailed in Greene and Wuts (1991). Ester cleavage, as previously described, affords the hydrocinnamic acid (XVI).

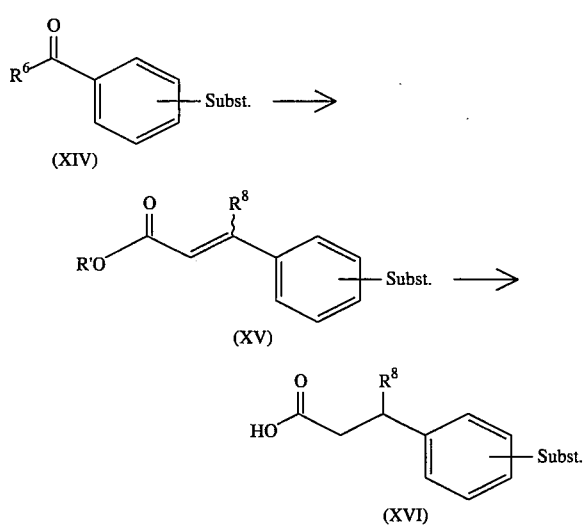

Scheme 3

(XIV)

(XV)

(XVI)

The symmetrical bis-benzylated acetic acids (XX) (Table 1) can be prepared according to Scheme 4.

Scheme 4

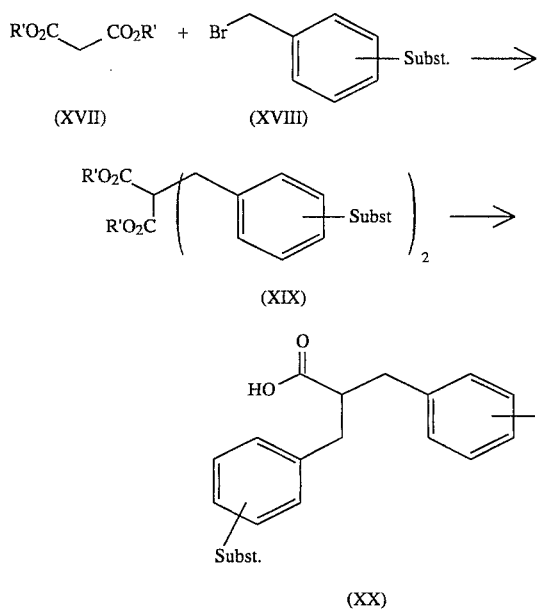

Bisalkylation of diester (XVII) using a strong non-nucleophilic base, preferrably sodium hydride, and the bromide (XVIII) gives diester (XIX), which can be hydrolyzed and decarboxylated using alkaline hydroxide and heat to the acid (XX).

The substituted phenoxyacetic acids (Table 1) are prepared by the general route shown in Scheme 5. The substituted phenols (XXI) are deprotonated with a strong base, preferrably sodium hydride, and then alkylated with the appropriate bromoacetate (XXII) to give (XXIII). Ester cleavage using an above described method can provide the acid (XXIV).

Scheme 5

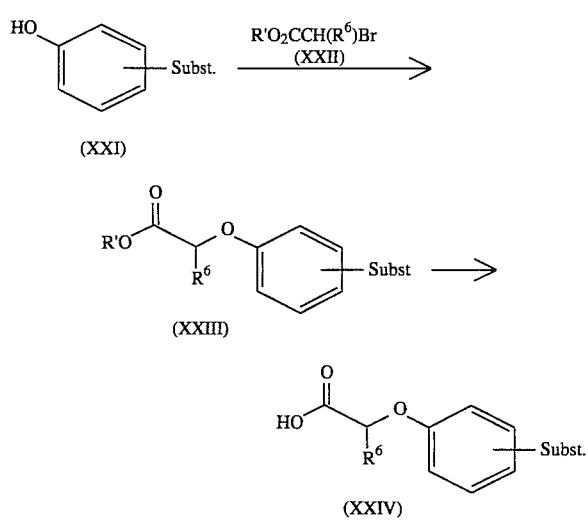

The substituted thiophenoxyacetic acids (Table 1) are prepared by a similar route as shown in Scheme 6.

Scheme 6

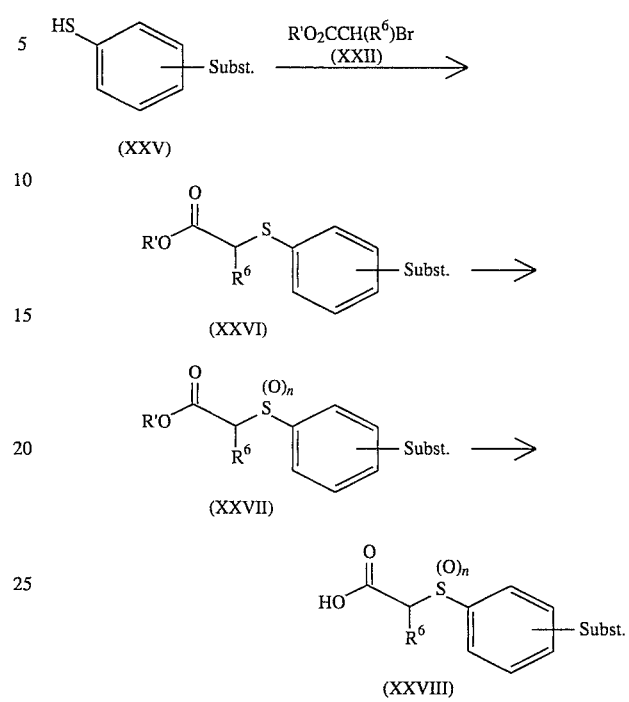

Thus, deprotonation of thiophenol (XXV) and alkylation according to Scheme 4 affords (XXVI). Ester cleavage then gives the thiophenoxyacetic acid (XXVIII, n=0). Alternatively, the sulfur can be oxidized by 1 or 2 equivalents of sodium periodate or other suitable oxidizing agent to give the corresponding sulfoxide (XXVIII, n=1) or sulfone (XXVIII, n=2), respectively.

The α,α-dimethylphenoxy- or α,α-dimethylthiophenoxy acetic acids (XXXI) (Table 1) can be prepared according to Scheme 7. The phenol or thiophenol (XXIX) can be treated with 2-trichloromethyl-2-propanol (XXX) in the presence of sodium hydroxide, according to the method of Corey et. al. *J. Am Chem Soc.* 91, 4782 (1969) to produce the acid (XXXI).

Scheme 7

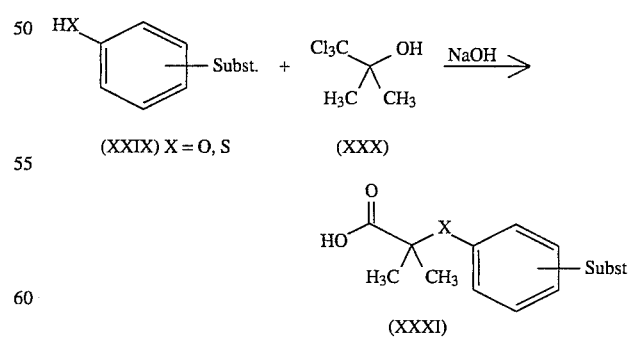

The diphenylmethane derivatives 35 (Table 3) are prepared as outlined in Scheme 8.

Scheme 8

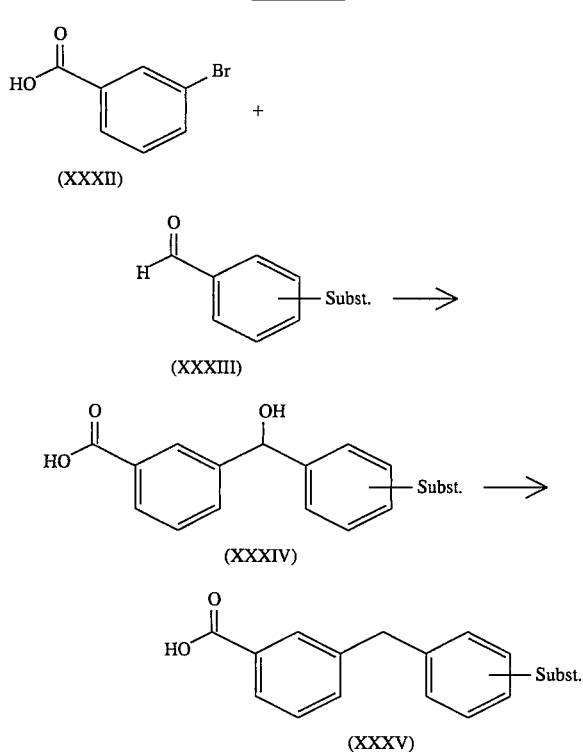

The dianion of 3-bromobenzoic acid (XXXII) (Parham et. al. *J. Org. Chem* 39, 2051 (1974)), prepared by sequential treatment with 1 eq of n-butyllithium and 2 eq of t-butyllithium at −78° C., is allowed to react with aldehyde (XXXIII) to give alcohol (XXXIV). This alcohol can be reductively deoxygenated to the methylene adduct (XXXV) by a number of methods; the preferred methods include reduction with triethylsilane in trifluoroacetic acid, according to the method of Doyle et. al. *J. Org. Chem.* 38, 2675 (1973), or reduction with sodium cyanoborohydride in the presence of zinc iodide, according to the method described in Lau et. al. *J. Org. Chem.* 51, 3038 (1986).

The diphenylsulfides (XL) and diphenylsulfoxides (XLI) (Table 3) are prepared according to Scheme 9.

Scheme 9

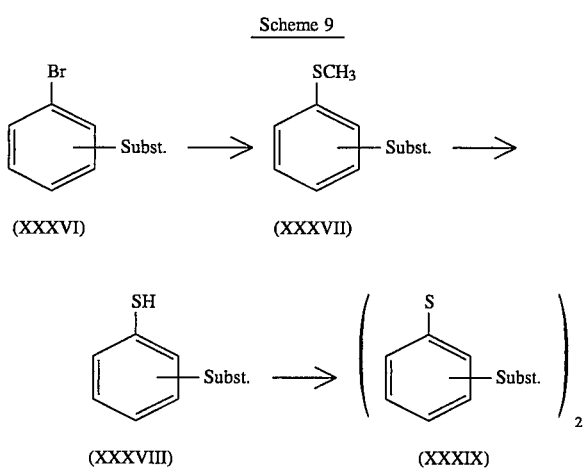

-continued
Scheme 9

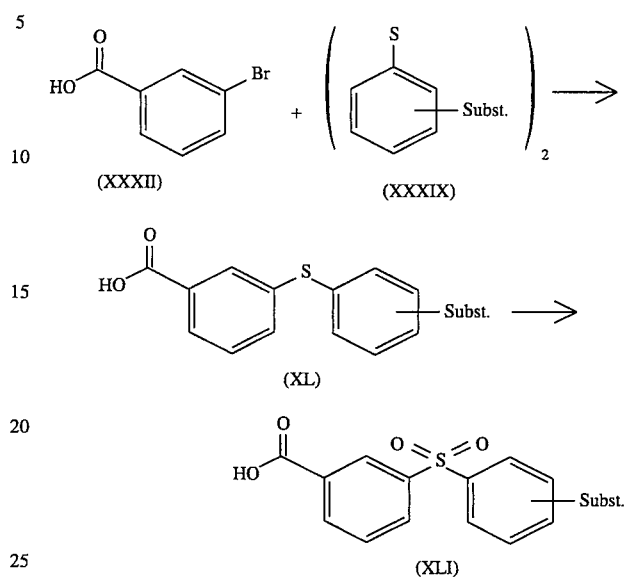

When the thiophenol (XXXVIII) was not commercially available, it can be readily prepared from bromide (XXXVI). Metallation with t-butyllithium followed by trapping with dimethyldisulfide can provide (XXXVII), provided that the functionality substituted on the aryl is compatible to the reaction conditions or is suitably protected to withstand such conditions. Oxidation followed by Pummerer rearrangement and methanolysis affords the substituted thiophenol (XXXVIII), based on that reported by Young et. al. Tetrahedron Lett. 25, 1753 (1984). The corresponding disulfide (XXXIX) can readily prepared by air oxidation of (XXXVIII). The dianion of bromobenzoic acid (XXXII), similar to Scheme 8, can be trapped with disulfide (XXXIX) to afford sulfide (XL). When the sulfone (XLI) is desired, it can readily prepared by oxone oxidation of sulfide (XL), according to the method of Trost et. al. *Tetrahedron Lett.* 22, 1287 (1981).

The 4-arylpyrrolidine-3-carboxylic acids (Table 5) are prepared according to Scheme 10 by [3+2] cycloaddition of olefin (XLII) with an N-benzyl azomethine ylide which can be generated in situ in two different ways.

Scheme 10

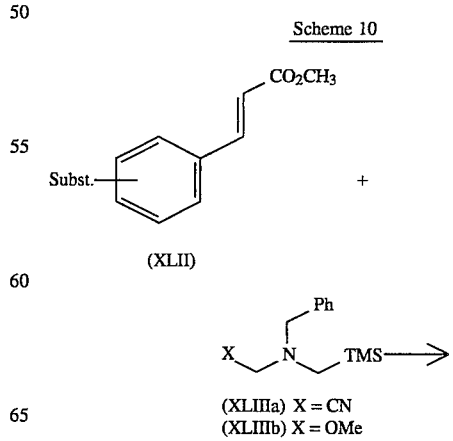

-continued
Scheme 10

(XLIV)

(XLV)

PG is a suitable amine protecting group

The preferred method involves treating N-benzyl-N-(methoxymethyl)trimethylsilylmethylamine (XLIIIb) with trifluoroacetic acid, according to the method of Achiwa et. al. *Chem. Pharm. Bull.* 33, 2762 (1985). Alternatively, N-benzyl-N-(cyanomethyl)trimethylsilylmethylamine (XLIIIa) can be treated with silver fluoride in the dark, according to the method of Padwa et. al. *J. Org. Chem.* 50, 4006 (1985). Generation of the azomethine ylide by either method and reaction with (XLII) affords the pyrrolidine (XLIV). Manipulation of the amine-protectiong group to give a more versatile carbamate-protected (CBZ or t-BOC) pyrrolidine followed by ester hydrolysis using alkaline hydrolysis can provide the carboxylic acid (XLV).

The 2-phenylcyclohexane carboxylic acids (Table 5) can be prepared according to Scheme 11. Ketoester (XLVI) can be converted into its corresponding enol trifluoromethanesulfonate and subsequently coupled with phenylboric acid under palladium catalysis, according to the method of Suzuki et. al. *Syn. Commun.* 11, 513 (1981) to afford (XLVII). Catalytic hydrogenation using the conditions previously described gives cis-(XLVIII), which can readily be isomerized to trans-(XLVIII) upon treatment with alkoxide in an alcoholic solvent. Ester hydrolysis as described above using alkoxide in an aqueous alcoholic solvent mixture can provide the acid (IL) of either stereoisomer.

Scheme 11

(XLVI)    (XLVII)

(XLVIII)   (IL)

The cyclic urea analogs (Table 6) are prepared according to Scheme 12. Condensation of 1,2-phenylenediamine (L) with ethyl acetoacetate (LI) in a high boiling solvent such as xylene gives the unusual isopropenyl substituted (LII) based on the described by Davoll *J. Chem. Soc.* p. 308 (1960).

N-alkylation with ethyl bromoacetate using a strong base, preferrably sodium hydride, can provide (LIII), wherein R=C(=CH$_2$)CH$_3$), which gives the corresponding acid (LIV) upon ester hydrolysis using mineral acid. Ultimately this residue can be reduced to an isopropyl substituent in the final boropeptide of formula (I). Alternatively, N-alkylation of (LII) as above followed by sulfuric acid hydrolysis gives (LIII), wherein R=H. This intermediate can be carried on directly to (LIV), wherein R=H or N-alkylated prior to ester hydrolysis to give N-alkyl derivatives.

Scheme 12

(L)   (LI)

(LII)

(LIII)
R = H, C(=CH$_2$)CH$_3$ (LIV)
R = Me, Et        (steps b–e); H (steps b, c, e);
C(=CH$_2$)CH$_3$   (steps b, e)

Using the procedures described in Schemes 1–12 above and other standard procedures known to those skilled in the art of organic synthesis, the compounds of this invention listed in Tables 1–10 were or can be prepared.

EXAMPLES

Example 4

Ph(CH$_2$)$_2$C(=O)Pro-boroArg-OH.hydrochloride salt

Part A: Preparation of Ph(CH$_2$)$_2$C(=O)Pro-OBn

To a cooled (0° C.) solution of hydrocinnamic acid (2.0 g, 13.3 mmol) in THF (40 mL) was added Et$_3$N (3.71 mL, 26.6 mmol) followed by isobutyl chloroformate (1.73 mL, 1.82 g, 13.3 mmol). The mixture was stirred for 15 min at which time L-Proline benzyl ester hydrochloride (3.22 g, 13.3 mmol) was added. The mixture was stirred with warming to 25° C. for 2 h. The solvent was removed in vacuo, the residue was diluted with EtOAc and washed with 10% aq HCl, sat'd aq NaHCO$_3$ and brine. After drying (Na$_2$SO$_4$), the solvent was removed and the residue was purified by flash chromatography to give the product (3.1 g). $^1$H NMR (CDCl$_3$) δ7.40–7.05 (m, 10H), 5.16 (q, 2H), 4.55 (dd, 1H), 3.55 (m, 1H), 3.37 (m, 1H), 2.97 (t, 2H), 2.60 (m, 2H), 2.20–1.80 (m, 4H).

Part B: Preparation of Ph(CH$_2$)$_2$C(=O)Pro-OH

To a solution of Ph(CH$_2$)$_2$C(=O)Pro-OBn (3.1 g, 9.1 mmol) in absolute MeOH (10 mL) was added 10% Pd/C catalyst (0.50 g). The mixture was stirred under 1 atm of hydrogen (H$_2$) at 25° C. for 16 h and then was filtered through Celite and concentrated to afford the product (2.2 g). $^1$H NMR (CDCl$_3$) δ7.35–7.10 (m, 5H), 4.57 (d, 1H), 3.45 (m, 1H), 3.30 (m, 1H), 3.00 (t, 2H), 2.65 (t, 2H), 2.30 (m, 1H), 1.97 (m, 3H).

Part C: Preparation of Ph(CH$_2$)$_2$C(=O)Pro-NH—CH[(CH$_2$)$_3$Br]BO$_2$—C$_{10}$H$_{16}$.

To a cooled (0° C.) solution of Ph(CH$_2$)$_2$C(=O)Pro-OH (0.50 g, 2.0 mmol) in THF (10 mL) was added N-methylmorpholine (0.22 mL, 2.0 mmol) followed by isobutyl chloroformate (0.26 mL, 2.0 mmol). The mixture was stirred for 15 min at which time H$_2$NCH[(CH$_2$)$_3$Br]BO$_2$—C$_{10}$H$_{16}$.HCl (0.74 g, 2.0 mmol) was added followed by Et$_3$N (0.7 mL, 5.1 mmol). The reaction was stirred with warming to 25° C. for 1.5 h and then the solvent was removed. The residue was diluted with EtOAc, washed with 10% aq HCl, sat'd aq NaHCO$_3$ and brine, dried (Na$_2$SO$_4$) and concentrated. The residue was purified by flash chromatography to give the product (0.22 g). MS: m/z 561 (M+H)+.

Part D: Preparation of Ph(CH$_2$)$_2$C(=O)Pro-NH—CH[(CH$_2$)$_3$N$_3$]BO$_2$—C$_{10}$H$_{16}$ To a solution of Ph(CH$_2$)$_2$C(=O)Pro-NH—CH[(CH$_2$)$_3$Br]BO$_2$—C$_{10}$H$_{16}$ (1.34 g, 2.39 mmol) in DMF (5 mL) was added sodium azide (0.31 g, 4.79 mmol). The solution was stirred at 100° C. for 2 h and then it was allowed to cool to 25° C. The mixture was diluted with EtOAc, washed with water (H$_2$O) and brine, dried (Na$_2$SO$_4$) and concentrated to afford the product. MS: m/z 522 (M+H)+.

Part E: Preparation of Ph(CH$_2$)$_2$C(=O)Pro-boroOrn-C$_{10}$H$_{16}$

To a solution of Ph(CH$_2$)$_2$C(=O)Pro-NH—CH[(CH$_2$)$_3$N$_3$]BO$_2$—C$_{10}$H$_{16}$ (0.27 g, 0.52 mmol) in MeOH (3 mL) was added 20% Pd(OH)$_2$/C catalyst (100 mg). The mixture was stirred under 1 atm of H$_2$ for 1 h and then filtered through Celite and concentrated to give the product (0.21 g).

Part F: Preparation of Ph(CH$_2$)$_2$C(=O)Pro-boroArg-C$_{10}$H$_{16}$.HCl

To a solution of Ph(CH$_2$)$_2$C(=O)Pro-boroOrn-C$_{10}$H$_{16}$ (0.21 g, 0.40 mmol) in ethanol (3 mL) was added (DMAP) (98 mg, 0.8 mmol) and formamidine sulfonic acid (100 mg, 0.8 mmol). The mixture was stirred at reflux for 3 h and then filtered through Celite. The solvent was removed in vacuo and th residue was purified by chromatography on a Sephadex LH-20 column (elution with MeOH) to afford 62 mg of material which was treated with anhydrous hydrogen chloride in Et$_2$O (1N) to obtain the title compound. MS: m/z 538 (M+H)+.

Part G: To a solution of Ph(CH$_2$)$_2$C(=O) Pro-boroArg-C$_{10}$H$_{16}$.HCl (150 mg, 0.26 mmol) in Et$_2$O (5 mL) and H2O (5 mL) was added phenylboric acid (160 mg, 1.3 mmol). This mixture was stirred at 25° C. for 3 h. The separated aqueous layer was washed with ether twice and the water was removed in vacuo to give 105 mg of the product. MS: m/z 358 (M+H(-BO$_2$H$_3$))+.

Example 5

Ph(CH$_2$)$_2$C(=O)Pro-boroLys-OH, hydrochloride

Part A: Preparation of Ph(CH$_2$)$_2$C(=O)Pro-NH—CH[(CH$_2$)$_4$Br]BO$_2$—C$_{10}$H$_{16}$ This compound was prepared by coupling the acid Ph(CH$_2$)$_2$C(=O)Pro-OH with the amine H$_2$NCH[(CH$_2$)$_4$Br]BO$_2$ —C$_{10}$H$_{16}$.HCl according to the procedure in Example 4, Part C. MS: m/z 536 (M+H)+.

Part B: Ph(CH$_2$)$_2$C(=O)Pro-NHCH[(CH$_2$)$_4$N$_3$]BO$_2$—C$_{10}$H$_{16}$

This compound was prepared from the bromide in Part A above according to the procedure in Example 4, Part D. MS: m/z 536 (M+H)+.

Part C: Ph(CH$_2$)$_2$C(=O)Pro-boroLys-C$_{10}$H$_{16}$.HCl

This compound was prepared from the azide in Part B above according to the procedure in Example 4, Part E. MS: m/z 510 (M+H)+.

Part D. Ph(CH$_2$)$_2$C(=O)Pro-boroLys-OH.HCl

This compound was prepared from the product in Part C above according to the procedure in Example 4, Part G. MS: m/z 340 (M+H(—ZH$_2$O))+.

Example 166

3-[2-CF$_3$C$_6$H$_4$CH$_2$]C$_6$H$_4$C(=O)Pro-boroLys-C$_{10}$H$_{16}$.hydrochloride Part A: Preparation of 3-[2-CF$_3$C$_6$H$_4$CH(OH)]C$_6$H$_4$CO$_2$H To a cooled (−78° C.) solution of 3-bromobenzoic acid (15.0 g, 74.6 mmol) in THF (300 mL) was added n-butyllithium (30.0 mL of a 2.5M solution in hexanes, 74.6 mmol) dropwise. This was followed by the dropwise addition of t-butyllithium (88.0 mL of a 1.7M solution in hexanes, 149.2 mmol). The solution was allowed to stir at −78° C. for 1 h and then α,α,α-trifluoro-o-tolualdehyde (13.0 g, 74.6 mmol) was added and the solution was maintained at −78° C. an additional 1 h. The solution was then allowed to warm to 25° C. and was quenched by the addition of 20 mL of sat'd aqueous NH$_4$Cl. The solvent was removed in vacuo and the residue was diluted with water and extracted with 1:1 hexane/ether. The organics were discarded. The aqueous layer was acidified with concentrated HCl and then extracted with ethyl acetate. The ethyl acetate extracts were washed with sat'd aqueous sodium chloride (NaCl), dried over magnesium sulfate (MgSO$_4$) and concentrated to give the crude product as a yellow oil. MS: m/z 314 (M+NH$_4$)+.

Part B: Preparation of 3-[2-CF$_3$C$_6$H$_4$CH(OH)]C$_6$H$_4$CO$_2$H

To a solution of 3-[2-CF$_3$C$_6$H$_4$CH(OH)]C$_6$H$_4$CO$_2$H (13.5 g, 45.8 mmol) in trifluoroacetic acid (50 mL) was added triethylsilane (30.0 mL, 183.3 mmol). This solution was allowed to stir at 25° C. for 24 h. The trifluoroacetic acid was removed in vacuo and the residue was taken up in 1M potassium hydroxide. This solution was extracted with 1:1 hexane/Et$_2$O. The organics were discarded. The aqueous layer was acidified with concentrated HCl and then extracted with ethyl acetate. The ethyl acetate extracts were washed with sat'd aqueous NaCl, dried (MgSO$_4$) and concentrated to give the product as a waxy yellow solid. MS: m/z 298.0 (M+NH$_4$)+.

Part C: The carboxylic acid 3-[2-CF$_3$C$_6$H$_4$CH$_2$]C$_6$H$_4$CO$_2$H was carried on according to the procedures described in Example 5, Parts A–D to afford the title compound.

Example 212 trans-[N—BOC-4-(3-(CF$_3$)C$_6$H$_4$)-3-(C=O)-pyrrolidinyl]
Pro-boroLys-C$_{10}$H$_{16}$, hydrochloride Part A: Preparation of (E)-3-(CF$_3$)C$_6$H$_4$CH=CHCO$_2$CH$_3$ To a solution of (E)-3-trifluoromethylcinnamic acid (5.6 g, 25.9 mmol) in absolute MeOH (50 mL) was added concentrated sulfuric acid (2 mL). The solution was stirred at reflux for 16 h and then was allowed to cool to 25° C. The solvent was removed in vacuo and the residue was diluted with EtOAc, washed with H$_2$O, sat'd aq NaHCO$_3$ and brine, dried (MgSO$_4$) and concentrated to give the ester as an oil.

Part B: Preparation of trans-[N-Benzyl-4-(3 -(CF$_3$)C$_6$H$_4$)-3-(C=O)-pyrrolidinyl]OCH$_3$.

To a solution of the product from Part A (3.25 g, 14.1 mmol) in acetonitrile (CH$_3$CN, 100 mL) was added N-benzyl trimethylsilylmethylaminoacetonitrile (3.27 g, 14.1 mmol) followed by silver fluoride (1.97 g, 15.5 mmol). This mixture was stirred in the dark at 25° C. for three days. The mixture was diluted with chloroform (CHCl$_3$), filtered through a pad of silica gel/Celite and concentrated. The residue was purified by flash chromatography (5:1 hexanes/EtOAc) to afford the product (2.6 g) as an oil. MS (NH$_3$/CI): m/z 364 (M+H)+.

Part C: Preparation of trans-[4-(3-(CF$_3$)C$_6$H$_4$)-3-(C=O)-pyrrolidinyl]OCH$_3$.HCl To a solution of trans-[N-Benzyl-4-(3-(CF$_3$)C$_6$H$_4$)-3-(C=O)-pyrrolidinyl]OCH$_3$ (2.6 g, 7.2 mmol) in absolute MeOH (50 mL) was added 10% Pd/C catalyst (0.26 g) and conc. HCl (0.60 mL, 7.2 mmol). This mixture was stirred under 1 atm of H$_2$ for 5 h and then was filtered through Celite and concentrated to give the product as a solid. MS (NH$_3$/CI): m/z 274 (M+H)+.

Part D: Preparation of trans-[N-BOC-4-(3-(CF$_3$)C$_6$H$_4$)-3-C=O)-pyrrolidinyl]OCH$_3$.

To a cooled (0° C.) solution of trans-[4-(3 -(CF$_3$)C$_6$H$_4$)-3-(C=O)-pyrrolidinyl]OCH$_3$.HCl (2.15 g, 6.94 mmol) in dichloromethane (CH$_2$Cl$_2$, 40 mL) was added di-tert-butyl dicarbonate (1.51 g, 6.94 mmol), diisopropylethylamine (2.42 mL, 13.9 mmol) and DMAP (0.21 g, 1.74 mmol). The resulting solution was allowed to warm to 25° C. and stirred 16 h. The solvent was removed in vacuo and the residue was diluted with 1:1 hexanes/EtOAc and then washed with 10% aq HCl, sat'd NaHCO$_3$ and brine. After drying (MgSO$_4$) the solution was filtered through a pad of silica gel and concentrated to afford the product as an oil. MS (NH$_3$/CI): m/z 374 (M+H)+.

Part E: Preparation of trans-[N-BOC-4-(3-(CF$_3$)C$_6$H$_4$)-3-(C=O)-pyrrolidinyl]OH.

To a solution of trans-[N-BOC-4-(3-(CF$_3$)C$_6$H$_4$)-3-(C=O)-pyrrolidinyl]OCH$_3$ (2.5 g, 6.7 mmol) in THF (20 mL) and H$_2$O (10 mL) was added lithium hydroxide hydrate (LiOH H$_2$O). The solution was stirred at 25° C. for 4 h at which time it was diluted with H$_2$O and extracted with 1:1 hexanes/EtOAc. The organics were discarded. The aqueous layer was acidified to pH 2 with 10% aq HCl and extracted with EtOAc. The organics were washed with brine, dried (MgSO$_4$) and concentrated to afford the product (2.3 g) as a white solid. MS (NH$_3$/CI): m/z 360 (M+H)+.

Part F: Preparation trans-[N-BOC-4-(3-(CF$_3$)C$_6$H$_4$)-3-(C=O)-pyrrolidinyl]Pro-OMe To a solution of trans-[N-BOC-4-(3-(CF$_3$)C$_6$H$_4$)-3-(C=O)-pyrrolidinyl]OH (1.52 g, 4.23 mmol) in DMF (10 mL) was added L-Proline methyl ester hydrochloride (0.70 g, 4.23 mmol), O-benzotriazol-1-yl-N,N,N',N'-tetramethyluronium hexafluorophospate (1.60 g, 4.23 mmol) and diisopropylethylamine (1.62 mL, 9.31 mmol). The resulting solution was stirred at 25° C. for three days. The mixture was diluted with EtOAc, washed with H$_2$O (2 times) and brine, dried (MgSO$_4$) and concentrated. The residue was purified by flash chromatography (1:1 hexanes/EtOAc) to afford the product as an oil. MS (NH$_3$/CI): m/z 471 (M+H)+.

Part G: Preparation of trans-[N-BOC-4-(3-(CF$_3$)C$_6$H$_4$)-3-(C=O)-pyrrolidinyl]Pro-OH.

To a solution of trans-[N-BOC-4-(3-(CF$_3$)C$_6$H$_4$)-3-(C=O)-pyrrolidinyl]Pro-OCH$_3$ (2.0 g, 4.24 mmol) in 20 mL of THF and 10 mL of H$_2$O was added LiOH.H$_2$O (0.20 g, 4.7 mmol). The resulting solution was stirred at 25° C. for 3 h and then was diluted with H$_2$O and extracted with 1:1 hexanes/EtOAc. The organics were discarded. The aqueous layer was acidified to pH 2 with 10% aq HCl and extracted with EtOAc. The organics were washed with brine, dried (MgSO$_4$) and concentrated to give the product as a white solid. MS (NH$_3$/CI): m/z 457 (M+H)+.

Part H: Preparation of trans-[N-BOC-4-(3-(CF$_3$)C$_6$H$_4$)-3-(C=O)-pyrrolidinyl]Pro-NHCH[(CH$_2$)$_4$Br]BO$_2$C$_{10}$H$_{16}$.

This compound was prepared by coupling the acid from Part G above with H$_2$NCH[(CH$_2$)$_4$Br]BO$_2$—C$_{10}$H$_{16}$.HCl according to the procedure in Example 4, Part C. MS (NH$_3$/CI): m/z 782/784 (M+H)+.

Part I: Preparation of trans-[N-BOC-4-(3-(CF$_3$)C$_6$H$_4$)-3-(C=O)-pyrrolidinyl]Pro-NH—CH[(CH$_2$)$_4$N$_3$]BO$_2$—C$_{10}$H$_{16}$.

This compound was prepared from the bromide in Part H above according to the procedure in Example 4, Part D. MS (NH$_3$/CI): m/z 745 (M+H)+.

Part J: This compound was prepared from the azide in Part I above according to the procedure in Example 4, Part E. MS (DCI): m/z 719 (M+H)+.

Example 213 trans-[4-(3-(CF$_3$)C$_6$H$_4$)-3-(C=O)-pyrrolidinyl]Pro-boroLys-C$_{10}$H$_{16}$, dihydrochloride To a solution of Example 195 (0.30 g, 0.40 mmol) was added 12N HCl (about 0.5 mL). This solution was stirred at 25° C. for 16 h. The mixture was partitioned between H$_2$O and EtOAc. The aqueous layer was washed with EtOAc and concentrated to afford the product as a white solid. MS (DCI): m/z 619 (M+H)+.

TABLE 1

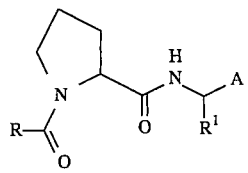

| Ex No. | R¹ | A | R | Phys Data |
|---|---|---|---|---|
| 1 | —(CH₂)₃SC(=NH)NH₂ | BO₂C₁₀H₁₆ | PhCH₂CH₂— | MS |
| 2 | —(CH₂)₃NHC(=NH)NH₂ | BO₂C₁₀H₁₆ | PhCH₂CH₂— | MS |
| 3 | —(CH₂)₄NH₂ | BO₂C₁₀H₁₆ | PhCH₂CH₂— | MS |
| 4 | —(CH₂)₃NHC(=NH)NH₂ | B(OH)₂ | PhCH₂CH₂— | MS |
| 5 | —(CH₂)₄NH₂ | B(OH)₂ | PhCH₂CH₂— | MS |
| 6 | —(CH₂)₃SC(=NH)NH₂ | BO₂C₁₀H₁₆ | 4-PhC₆H₄CH₂CH₂— | MS |
| 7 | —(CH₂)₄NH₂ | B(OH)₂ | 4-PhC₆H₄CH₂CH₂— | |
| 8 | —(CH₂)₃SC(=NH)NH₂ | BO₂C₁₀H₁₆ | 2-PhC₆H₄CH₂CH₂— | MS |
| 9 | —(CH₂)₄NH₂ | BO₂C₁₀H₁₆ | 2-PhC₆H₄CH₂CH₂— | MS |
| 10 | —(CH₂)₄NH₂ | B(OH)₂ | 3-PhC₆H₄CH₂CH₂— | |
| 11 | —(CH₂)₃SC(=NH)NH₂ | BO₂C₁₀H₁₆ | 2-OCH₃C₆H₄CH₂CH₂— | MS |
| 12 | —(CH₂)₄NH₂ | BO₂C₁₀H₁₆ | 2-OCH₃C₆H₄CH₂CH₂— | MS |
| 13 | —(CH₂)₄NH₂ | B(OH)₂ | 3-OCH₃C₆H₄CH₂CH₂— | |
| 14 | —(CH₂)₃SC(=NH)NH₂ | BO₂C₁₀H₁₆ | 4-OCH₃C₆H₄CH₂CH₂— | MS |
| 15 | —(CH₂)₄NH₂ | BO₂C₁₀H₁₆ | 4-OCH₃C₆H₄CH₂CH₂— | MS |
| 16 | —(CH₂)₄NH₂ | BO₂C₁₀H₁₆ | 3-CF₃C₆H₄CH₂CH₂— | MS |
| 17 | —(CH₂)₄NH₂ | B(OH)₂ | 3-CF₃C₆H₄CH₂CH₂— | MS |
| 18 | —(CH₂)₄NH₂ | BO₂C₁₀H₁₆ | 2-CF₃C₆H₄CH₂CH₂— | MS |
| 19 | —(CH₂)₄NH₂ | B(OH)₂ | 4-CF₃C₆H₄CH₂CH₂— | |
| 20 | —(CH₂)₄NH₂ | BO₂C₁₀H₁₆ | 3-CH₃C₆H₄CH₂CH₂— | MS |
| 21 | —(CH₂)₄NH₂ | B(OH)₂ | 3-CH₃C₆H₄CH₂CH₂— | MS |
| 22 | —(CH₂)₄NH₂ | BO₂C₁₀H₁₆ | 2-CH₃C₆H₄CH₂CH₂— | MS |
| 23 | —(CH₂)₄NH₂ | B(OH)₂ | 4-CH₃C₆H₄CH₂CH₂— | MS |
| 24 | —(CH₂)₄NH₂ | BO₂C₁₀H₁₆ | 4-OCH₃-3-CH₃C₆H₃CH₂CH₂— | MS |
| 25 | —(CH₂)₄NH₂ | BO₂C₁₀H₁₆ | 2,4-(CH₃)₂C₆H₃CH₂CH₂— | MS |
| 26 | —(CH₂)₄NH₂ | BO₂C₁₀H₁₆ | 3,4-(OCH₂O)C₆H₃CH₂CH₂— | MS |
| 27 | —(CH₂)₄NH₂ | B(OH)₂ | 2,3-(OCH₂O)C₆H₃CH₂CH₂— | |
| 28 | —(CH₂)₃SC(=NH)NH₂ | BO₂C₁₀H₁₆ | 4-(NHCO(CH₂)₃Ph)C₆H₄CH₂CH₂— | MS |
| 29 | —(CH₂)₄NH₂ | B(OH)₂ | 2-OHC₆H₄CH₂CH₂— | |
| 30 | —(CH₂)₄NH₂ | BO₂C₁₀H₁₆ | 3-OHC₆H₄CH₂CH₂— | MS |
| 31 | —(CH₂)₄NH₂ | B(OH)₂ | 4-OHC₆H₄CH₂CH₂— | |
| 32 | —(CH₂)₄NH₂ | B(OH)₂ | 2-(CO₂H)C₆H₄CH₂CH₂— | |
| 33 | —(CH₂)₄NH₂ | B(OH)₂ | 3-(CO₂H)C₆H₄CH₂CH₂— | |
| 34 | —(CH₂)₄NH₂ | BO₂C₁₀H₁₆ | 4-(CO₂H)C₆H₄CH₂CH₂— | MS |
| 35 | —(CH₂)₄NH₂ | B(OH)₂ | 2-(CO₂CH₃)C₆H₄CH₂CH₂— | |
| 36 | —(CH₂)₄NH₂ | B(OH)₂ | 3-(CO₂CH₃)C₆H₄CH₂CH₂— | |
| 37 | —(CH₂)₄NH₂ | B(OH)₂ | 4-(CO₂CH₃)C₆H₄CH₂CH₂— | |
| 38 | —(CH₂)₄NH₂ | B(OH)₂ | 2-(PhC(=O)NH)—C₆H₄CH₂CH₂— | |
| 39 | —(CH₂)₄NH₂ | B(OH)₂ | 3-(PhC(=O)NH)—C₆H₄CH₂CH₂— | |
| 40 | —(CH₂)₄NH₂ | B(OH)₂ | 4-(PhC(=O)NH)—C₆H₄CH₂CH₂— | |
| 41 | —(CH₂)₄NH₂ | B(OH)₂ | 2-NH₂C₆H₄CH₂CH₂— | |
| 42 | —(CH₂)₄NH₂ | B(OH)₂ | 3-NH₂C₆H₄CH₂CH₂— | |
| 43 | —(CH₂)₄NH₂ | B(OH)₂ | 4-NH₂C₆H₄CH₂CH₂— | |
| 44 | —(CH₂)₄NH₂ | B(OH)₂ | 2-(CH₂NH₂)C₆H₄CH₂CH₂— | |
| 45 | —(CH₂)₄NH₂ | B(OH)₂ | 3-(CH₂NH₂)C₆H₄CH₂CH₂— | |
| 46 | —(CH₂)₄NH₂ | B(OH)₂ | 4-(CH₂NH₂)C₆H₄CH₂CH₂— | |
| 47 | —(CH₂)₄NH₂ | B(OH)₂ | 2-CNC₆H₄CH₂CH₂— | |
| 48 | —(CH₂)₄NH₂ | B(OH)₂ | 3-CNC₆H₄CH₂CH₂— | |
| 49 | —(CH₂)₄NH₂ | B(OH)₂ | 4-CNC₆H₄CH₂CH₂— | |
| 50 | —(CH₂)₄NH₂ | B(OH)₂ | 2-FC₆H₄CH₂CH₂— | |
| 51 | —(CH₂)₄NH₂ | B(OH)₂ | 3-FC₆H₄CH₂CH₂— | |
| 52 | —(CH₂)₄NH₂ | B(OH)₂ | 4-FC₆H₄CH₂CH₂— | |
| 53 | —(CH₂)₃NHC(=NH)NH₂ | BO₂C₁₀H₁₆ | trans-PhCH=CH— | MS |

TABLE 1-continued

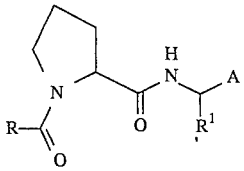

| Ex No. | R¹ | A | R | Phys Data |
|---|---|---|---|---|
| 54 | —(CH$_2$)$_4$NH$_2$ | B(OH)$_2$ | cis-PhCH=CH— | |
| 55 | —(CH$_2$)$_4$NH$_2$ | BO$_2$C$_{10}$H$_{16}$ | Ph$_2$CHCH$_2$— | MS |
| 56 | —(CH$_2$)$_4$NH$_2$ | BO$_2$C$_{10}$H$_{16}$ | (4-FC$_6$H$_4$CH$_2$)$_2$CH— | MS |
| 57 | —(CH$_2$)$_4$NH$_2$ | BO$_2$C$_{10}$H$_{16}$ | (4-OCH$_3$C$_6$H$_4$CH$_2$)$_2$CH— | MS |
| 58 | —(CH$_2$)$_4$NH$_2$ | BO$_2$C$_{10}$H$_{16}$ | (3-CH$_3$C$_6$H$_4$CH$_2$)$_2$CH— | MS |
| 59 | —(CH$_2$)$_4$NH$_2$ | BO$_2$C$_{10}$H$_{16}$ | PhCH(CH$_3$)CH$_2$— | MS |
| 60 | —(CH$_2$)$_4$NH$_2$ | BO$_2$C$_{10}$H$_{16}$ | PhCH(CH$_2$CO$_2$H)CH$_2$— | MS |
| 61 | —(CH$_2$)$_4$NH$_2$ | BO$_2$C$_{10}$H$_{16}$ | 2-PhC$_6$H$_4$CH(CH$_3$)CH$_2$— | MS |
| 62 | —(CH$_2$)$_3$NHC(=NH)NH$_2$ | BO$_2$C$_{10}$H$_{16}$ | PhOCH$_2$— | MS |
| 63 | —(CH$_2$)$_3$NHC(=NH)NH$_2$ | B(OH)$_2$ | PhOCH$_2$— | MS |
| 64 | —(CH$_2$)$_4$NH$_2$ | BO$_2$C$_{10}$H$_{16}$ | PhOCH$_2$— | MS |
| 65 | —(CH$_2$)$_4$NH$_2$ | B(OH)$_2$ | PhOCH$_2$— | MS |
| 66 | —(CH$_2$)$_3$NHC(=NH)NH$_2$ | BO$_2$C$_{10}$H$_{16}$ | 4-FC$_6$H$_4$OCH$_2$— | MS |
| 67 | —(CH$_2$)$_3$NHC(=NH)NH$_2$ | B(OH)$_2$ | 4-FC$_6$H$_4$OCH$_2$— | MS |
| 68 | —(CH$_2$)$_4$NH$_2$ | BO$_2$C$_{10}$H$_{16}$ | 4-FC$_6$H$_4$OCH$_2$— | MS |
| 69 | —(CH$_2$)$_4$NH$_2$ | B(OH)$_2$ | 4-FC$_6$H$_4$OCH$_2$— | MS |
| 70 | —(CH$_2$)$_3$NHC(=NH)NH$_2$ | BO$_2$C$_{10}$H$_{16}$ | 4-ClC$_6$H$_4$OCH$_2$— | MS |
| 71 | —(CH$_2$)$_4$NH$_2$ | BO$_2$C$_{10}$H$_{16}$ | 4-ClC$_6$H$_4$OCH$_2$— | MS |
| 72 | —(CH$_2$)$_4$NH$_2$ | B(OH)$_2$ | 2-CF$_3$C$_6$H$_4$OCH$_2$— | |
| 73 | —(CH$_2$)$_4$NH$_2$ | BO$_2$C$_{10}$H$_{16}$ | 3-CF$_3$C$_6$H$_4$OCH$_2$— | MS |
| 74 | —(CH$_2$)$_4$NH$_2$ | BO$_2$C$_{10}$H$_{16}$ | 4-CF$_3$C$_6$H$_4$OCH$_2$— | MS |
| 75 | —(CH$_2$)$_4$NH$_2$ | B(OH)$_2$ | 2-OCF$_3$C$_6$H$_4$OCH$_2$— | |
| 76 | —(CH$_2$)$_4$NH$_2$ | BO$_2$C$_{10}$H$_{16}$ | 3-OCF$_3$C$_6$H$_4$OCH$_2$— | MS |
| 77 | —(CH$_2$)$_4$NH$_2$ | BO$_2$C$_{10}$H$_{16}$ | 4-OCF$_3$C$_6$H$_4$OCH$_2$— | MS |
| 78 | —(CH$_2$)$_4$NH$_2$ | B(OH)$_2$ | 2-(CH$_2$CO$_2$CH$_3$)C$_6$H$_4$OCH$_2$— | |
| 79 | —(CH$_2$)$_4$NH$_2$ | BO$_2$C$_{10}$H$_{16}$ | 3-(CH$_2$CO$_2$CH$_3$)C$_6$H$_4$OCH$_2$— | MS |
| 80 | —(CH$_2$)$_4$NH$_2$ | B(OH)$_2$ | 4-(CH$_2$CO$_2$CH$_3$)C$_6$H$_4$OCH$_2$— | |
| 81 | —(CH$_2$)$_4$NH$_2$ | B(OH)$_2$ | 2-(CH$_2$CO$_2$H)C$_6$H$_4$OCH$_2$— | |
| 82 | —(CH$_2$)$_4$NH$_2$ | BO$_2$C$_{10}$H$_{16}$ | 3-(CH$_2$CO$_2$H)C$_6$H$_4$OCH$_2$— | MS |
| 83 | —(CH$_2$)$_4$NH$_2$ | BO$_2$C$_{10}$H$_{16}$ | 4-(CH$_2$CO$_2$H)C$_6$H$_4$OCH$_2$— | MS |
| 84 | —(CH$_2$)$_4$NH$_2$ | BO$_2$C$_{10}$H$_{16}$ | 3-(CH$_2$OTHP)C$_6$H$_4$OCH$_2$— | MS |
| 85 | —(CH$_2$)$_4$NH$_2$ | B(OH)$_2$ | 3-(CH$_2$OTHP)C$_6$H$_4$OCH$_2$— | MS |
| 86 | —(CH$_2$)$_4$NH$_2$ | B(OH)$_2$ | 2-(CH$_2$OH)C$_6$H$_4$OCH$_2$— | |
| 87 | —(CH$_2$)$_4$NH$_2$ | BO$_2$C$_{10}$H$_{16}$ | 3-(CH$_2$OH)C$_6$H$_4$OCH$_2$— | MS |
| 88 | —(CH$_2$)$_4$NH$_2$ | B(OH)$_2$ | 3-(CH$_2$OH)C$_6$H$_4$OCH$_2$— | MS |
| 89 | —(CH$_2$)$_3$SC(=NH)NH$_2$ | BO$_2$C$_{10}$H$_{16}$ | 3-(CH$_2$OH)C$_6$H$_4$OCH$_2$— | MS |
| 90 | —(CH$_2$)$_4$NH$_2$ | B(OH)$_2$ | 4-(CH$_2$OH)C$_6$H$_4$OCH$_2$— | |
| 91 | —(CH$_2$)$_4$NH$_2$ | B(OH)$_2$ | 2-(COCH$_3$)C$_6$H$_4$OCH$_2$— | |
| 92 | —(CH$_2$)$_4$NH$_2$ | B(OH)$_2$ | 3-(COCH$_3$)C$_6$H$_4$OCH$_2$— | |
| 93 | —(CH$_2$)$_4$NH$_2$ | BO$_2$C$_{10}$H$_{16}$ | 4-(COCH$_3$)C$_6$H$_4$OCH$_2$— | MS |
| 94 | —(CH$_2$)$_4$NH$_2$ | B(OH)$_2$ | 4-(COCH$_3$)C$_6$H$_4$OCH$_2$— | MS |
| 95 | —(CH$_2$)$_4$NH$_2$ | BO$_2$C$_{10}$H$_{16}$ | 2-PhC$_6$H$_4$OCH$_2$— | MS |
| 96 | —(CH$_2$)$_4$NH$_2$ | B(OH)$_2$ | 3-PhC$_6$H$_4$OCH$_2$— | |
| 97 | —(CH$_2$)$_4$NH$_2$ | B(OH)$_2$ | 4-PhC$_6$H$_4$OCH$_2$— | |
| 98 | —(CH$_2$)$_4$NH$_2$ | B(OH)$_2$ | 2-(CO$_2$CH$_3$)C$_6$H$_4$OCH$_2$— | |
| 99 | —(CH$_2$)$_4$NH$_2$ | BO$_2$C$_{10}$H$_{16}$ | 3-(CO$_2$CH$_3$)C$_6$H$_4$OCH$_2$— | MS |
| 100 | —(CH$_2$)$_4$NH$_2$ | B(OH)$_2$ | 4-(CO$_2$CH$_3$)C$_6$H$_4$OCH$_2$— | |
| 101 | —(CH$_2$)$_4$NH$_2$ | B(OH)$_2$ | 2-(CO$_2$H)C$_6$H$_4$OCH$_2$— | |
| 102 | —(CH$_2$)$_4$NH$_2$ | BO$_2$C$_{10}$H$_{16}$ | 3-(CO$_2$H)C$_6$H$_4$OCH$_2$— | MS |
| 103 | —(CH$_2$)$_4$NH$_2$ | BO$_2$C$_{10}$H$_{16}$ | 4-(CO$_2$H)C$_6$H$_4$OCH$_2$— | MS |
| 104 | —(CH$_2$)$_4$NH$_2$ | BO$_2$C$_{10}$H$_{16}$ | 4-ClC$_6$H$_4$OC(CH$_3$)$_2$— | MS |
| 105 | —(CH$_2$)$_3$NHC(=NH)NH$_2$ | BO$_2$C$_{10}$H$_{16}$ | PhOCH(CH$_2$CH$_3$)— | MS |
| 106 | —(CH$_2$)$_4$NH$_2$ | BO$_2$C$_{10}$H$_{16}$ | PhOCH(CH$_2$CH$_3$)— | MS |
| 108 | —(CH$_2$)$_4$NH$_2$ | B(OH)$_2$ | PhOCH(CH$_2$CH$_3$)— | MS |
| 109 | —(CH$_2$)$_4$NH$_2$ | BO$_2$C$_{10}$H$_{16}$ | PhOC(CH$_3$)$_2$— | MS |
| 110 | —(CH$_2$)$_4$NH$_2$ | B(OH)$_2$ | PhOC(CH$_3$)$_2$— | MS |
| 111 | —(CH$_2$)$_4$NH$_2$ | B(OH)$_2$ | PhOC(CH$_3$)$_2$— | MS |
| 112 | —(CH$_2$)$_3$NHC(=NH)NH$_2$ | BO$_2$C$_{10}$H$_{16}$ | PhOCH(CH$_3$)— | MS |
| 113 | —(CH$_2$)$_4$NH$_2$ | BO$_2$C$_{10}$H$_{16}$ | PhOCH(CH$_3$)— | MS |
| 114 | —(CH$_2$)$_4$NH$_2$ | B(OH)$_2$ | PhOCH(CH$_3$)— | MS |
| 115 | —(CH$_2$)$_4$NH$_2$ | BO$_2$C$_{10}$H$_{16}$ | (PhO)$_2$CH— | MS |
| 116 | —(CH$_2$)$_4$NH$_2$ | BO$_2$C$_{10}$H$_{16}$ | PhSCH$_2$— | MS |
| 117 | —(CH$_2$)$_4$NH$_2$ | B(OH)$_2$ | PhSCH$_2$— | MS |
| 118 | —(CH$_2$)$_3$NHC(=NH)NH$_2$ | BO$_2$C$_{10}$H$_{16}$ | PhSCH$_2$— | MS |
| 119 | —(CH$_2$)$_3$NHC(=NH)NH$_2$ | B(OH)$_2$ | PhSCH$_2$— | MS |

TABLE 1-continued

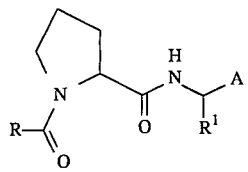

| Ex No. | R¹ | A | R | Phys Data |
|---|---|---|---|---|
| 120 | —(CH$_2$)$_4$NH$_2$ | BO$_2$C$_{10}$H$_{16}$ | PhSC(CH$_3$)$_2$— | MS |
| 121 | —(CH$_2$)$_4$NH$_2$ | BO$_2$C$_{10}$H$_{16}$ | PhSOCH$_2$— | MS |
| 122 | —(CH$_2$)$_4$NH$_2$ | BO$_2$C$_{10}$H$_{16}$ | 4-(NHCOCH$_3$)C$_6$H$_4$SCH$_2$— | MS |
| 123 | —(CH$_2$)$_4$NH$_2$ | B(OH)$_2$ | 4-(NHCOCH$_3$)C$_6$H$_4$SCH$_2$— | MS |
| 124 | —(CH$_2$)$_4$NH$_2$ | BO$_2$C$_{10}$H$_{16}$ | PhSO$_2$CH$_2$— | MS |
| 125 | —(CH$_2$)$_4$NH$_2$ | B(OH)$_2$ | PhSO$_2$CH$_2$— | MS |
| 126 | —(CH$_2$)$_3$SC(=NH)NH$_2$ | BO$_2$C$_{10}$H$_{16}$ | PhSO$_2$CH$_2$— | MS |
| 127 | —(CH$_2$)$_3$NHC(=NH)NH$_2$ | BO$_2$C$_{10}$H$_{16}$ | 4-(NHCBZ)C$_6$H$_4$CH$_2$— | MS |
| 128 | —(CH$_2$)$_3$NHC(=NH)NH$_2$ | BO$_2$C$_{10}$H$_{16}$ | 4-NH$_2$C$_6$H$_4$CH$_2$— | MS |
| 129 | —(CH$_2$)$_3$NHC(=NH)NH$_2$ | BO$_2$C$_{10}$H$_{16}$ | 3,4-(Cl)$_2$C$_6$H$_3$CH$_2$— | MS |
| 130 | —(CH$_2$)$_3$NHC(=NH)H | B(OH)$_2$ | 3,4-(Cl)$_2$C$_6$H$_3$CH$_2$— | MS |
| 131 | —(CH$_2$)$_3$NHC(=NH)NHCH$_3$ | B(OH)$_2$ | 3,4-(Cl)$_2$C$_6$H$_3$CH$_2$— | MS |
| 132 | —(CH$_2$)$_3$SC(=NH)NH$_2$ | BO$_2$C$_{10}$H$_{16}$ | PhCH(CH$_2$CH$_3$)— | MS |
| 133 | —(CH$_2$)$_4$NH$_2$ | BO$_2$C$_{10}$H$_{16}$ | 2-PhC$_6$H$_4$CH$_2$ | MS |
| 134 | —(CH$_2$)$_4$NH$_2$ | B(OH)$_2$ | 3-PhC$_6$H$_4$CH$_2$— | |
| 135 | —(CH$_2$)$_4$NH$_2$ | B(OH)$_2$ | 4-PhC$_6$H$_4$CH$_2$— | |
| 136 | —(CH$_2$)$_3$NHC(=NH)NH$_2$ | BO$_2$C$_{10}$H$_{16}$ | PhCH$_2$— | MS |
| 137 | —(CH$_2$)$_3$SC(=NH)NH$_2$ | BO$_2$C$_{10}$H$_{16}$ | Ph(CH$_2$)$_4$CH$_2$— | MS |
| 138 | —(CH$_2$)$_3$SC(=NH)NH$_2$ | BO$_2$C$_{10}$H$_{16}$ | CH$_3$(CH$_2$)$_3$CH$_2$— | MS |
| 139 | —(CH$_2$)$_4$NH$_2$ | BO$_2$C$_{10}$H$_{16}$ | CH$_3$(CH$_2$)$_3$CH$_2$— | MS |
| 140 | —(CH$_2$)$_3$SC(=NH)NH$_2$ | BO$_2$C$_{10}$H$_{16}$ | (CH$_3$)$_2$CHCH$_2$CH$_2$— | MS |
| 141 | —(CH$_2$)$_4$NH$_2$ | BO$_2$C$_{10}$H$_{16}$ | (CH$_3$)$_2$CHCH$_2$CH$_2$— | MS |
| 142 | —(CH$_2$)$_3$SC(=NH)NH$_2$ | BO$_2$C$_{10}$H$_{16}$ | CH$_3$CH$_2$CH(CH$_3$)CH$_2$— | MS |
| 143 | —(CH$_2$)$_3$SC(=NH)NH$_2$ | BO$_2$C$_{10}$H$_{16}$ | Ph(CH$_2$)$_3$CH$_2$— | MS |
| 144 | —(CH$_2$)$_4$NH$_2$ | BO$_2$C$_{10}$H$_{16}$ | C$_6$H$_{11}$CH$_2$CH$_2$— | MS |
| 145 | —(CH$_2$)$_4$NH$_2$ | BO$_2$C$_{10}$H$_{16}$ | (CH$_3$)$_2$CH(CH$_2$)$_2$CH$_2$— | MS |
| 146 | —(CH$_2$)$_4$NH$_2$ | BO$_2$C$_{10}$H$_{16}$ | C$_5$H$_9$CH$_2$CH$_2$— | MS |
| 147 | —(CH$_2$)$_3$SC(=NH)NH$_2$ | BO$_2$C$_{10}$H$_{16}$ | PhCH$_2$OCH$_2$— | MS |
| 148 | —(CH$_2$)$_4$NH$_2$ | BO$_2$C$_{10}$H$_{16}$ | C$_6$H$_{11}$OCH$_2$— | MS |
| 149 | —(CH$_2$)$_3$NHC(=NH)NH$_2$ | BO$_2$C$_{10}$H$_{16}$ | PhOCH$_2$CH$_2$— | MS |
| 150 | —(CH$_2$)$_3$NHC(=NH)H | BO$_2$C$_{10}$H$_{16}$ | 3,4-(Cl)$_2$C$_6$H$_3$CH$_2$— | MS |
| 151 | —(CH$_2$)$_3$NHC(=NH)NHCH$_3$ | BO$_2$C$_{10}$H$_{16}$ | 3,4-(Cl)$_2$C$_6$H$_3$CH$_2$— | MS |

TABLE 2

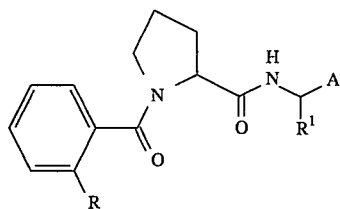

| Ex No. | R¹ | A | R | Phys Data |
|---|---|---|---|---|
| 152 | —(CH$_2$)$_4$NH$_2$ | BO$_2$C$_{10}$H$_{16}$ | PhO— | MS |
| 153 | —(CH$_2$)$_4$NH$_2$ | BO$_2$C$_{10}$H$_{16}$ | PhCH$_2$— | MS |
| 154 | —(CH$_2$)$_4$NH$_2$ | BO$_2$C$_{10}$H$_{16}$ | Ph— | MS |
| 155 | —(CH$_2$)$_3$SC(=NH)NH$_2$ | BO$_2$C$_{10}$H$_{16}$ | Ph— | MS |
| 156 | —(CH$_2$)$_3$NHC(=NH)H | BO$_2$C$_{10}$H$_{16}$ | PhCH$_2$— | MS |
| 157 | —(CH$_2$)$_3$NHC(=NH)H | B(OH)$_2$ | PhCH$_2$— | MS |
| 158 | —(CH$_2$)$_3$NHC(=NH)NHCH$_3$ | BO$_2$C$_{10}$H$_{16}$ | PhCH$_2$— | MS |
| 159 | —(CH$_2$)$_3$NHC(=NH)NHCH$_3$ | B(OH)$_2$ | PhCH$_2$— | MS |

TABLE 3

| Ex No. | R¹ | A | R | Data |
|---|---|---|---|---|
| 160 | —(CH$_2$)$_4$NH$_2$ | BO$_2$C$_{10}$H$_{16}$ | PhO— | MS |
| 161 | —(CH$_2$)$_4$NH$_2$ | B(OH)$_2$ | 2-FC$_6$H$_4$CH$_2$— | |
| 162 | —(CH$_2$)$_4$NH$_2$ | BO$_2$C$_{10}$H$_{16}$ | 3-FC$_6$H$_4$CH$_2$— | MS |
| 163 | —(CH$_2$)$_4$NH$_2$ | B(OH)$_2$ | 4-FC$_6$H$_4$CH$_2$— | |
| 164 | —(CH$_2$)$_4$NH$_2$ | BO$_2$C$_{10}$H$_{16}$ | PhCH$_2$— | MS |
| 165 | —(CH$_2$)$_4$NH$_2$ | B(OH)$_2$ | PhCH$_2$— | MS |
| 166 | —(CH$_2$)$_4$NH$_2$ | BO$_2$C$_{10}$H$_{16}$ | 2-CF$_3$C$_6$H$_4$CH$_2$— | MS |
| 167 | —(CH$_2$)$_4$NH$_2$ | BO$_2$C$_{10}$H$_{16}$ | 3-CF$_3$C$_6$H$_4$CH$_2$— | MS |
| 168 | —(CH$_2$)$_4$NH$_2$ | BO$_2$C$_{10}$H$_{16}$ | 4-CF$_3$C$_6$H$_4$CH$_2$— | MS |
| 169 | —(CH$_2$)$_4$NH$_2$ | B(OH)$_2$ | 2,3-(OCH$_2$O)C$_6$H$_3$CH$_2$— | |
| 170 | —(CH$_2$)$_4$NH$_2$ | BO$_2$C$_{10}$H$_{16}$ | 3,4-(OCH$_2$O)C$_6$H$_3$CH$_2$— | MS |
| 171 | —(CH$_2$)$_4$NH$_2$ | BO$_2$C$_{10}$H$_{16}$ | 3,4-(OCH$_3$)$_2$C$_6$H$_3$CH$_2$— | MS |
| 172 | —(CH$_2$)$_4$NH$_2$ | BO$_2$C$_{10}$H$_{16}$ | 2-CH$_3$C$_6$H$_4$CH$_2$— | MS |
| 173 | —(CH$_2$)$_4$NH$_2$ | B(OH)$_2$ | 3-CH$_3$C$_6$H$_4$CH$_2$— | |
| 174 | —(CH$_2$)$_4$NH$_2$ | B(OH)$_2$ | 4-CH$_3$C$_6$H$_4$CH$_2$— | |
| 175 | —(CH$_2$)$_4$NH$_2$ | B(OH)$_2$ | 2-OCH$_3$C$_6$H$_4$CH$_2$— | |
| 176 | —(CH$_2$)$_4$NH$_2$ | B(OH)$_2$ | 3-OCH$_3$C$_6$H$_4$CH$_2$— | |
| 177 | —(CH$_2$)$_4$NH$_2$ | B(OH)$_2$ | 4-OCH$_3$C$_6$H$_4$CH$_2$— | |
| 178 | —(CH$_2$)$_4$NH$_2$ | BO$_2$C$_{10}$H$_{16}$ | 2-BrC$_6$H$_4$CH$_2$— | MS |
| 179 | —(CH$_2$)$_4$NH$_2$ | BO$_2$C$_{10}$H$_{16}$ | 2-SCH$_3$C$_6$H$_4$CH$_2$— | MS |
| 180 | —(CH$_2$)$_4$NH$_2$ | BO$_2$C$_{10}$H$_{16}$ | PhS— | MS |
| 181 | —(CH$_2$)$_4$NH$_2$ | BO$_2$C$_{10}$H$_{16}$ | PhSO$_2$— | MS |
| 182 | —(CH$_2$)$_4$NH$_2$ | B(OH)$_2$ | PhS— | MS |
| 183 | —(CH$_2$)$_4$NH$_2$ | B(OH)$_2$ | PhSO$_2$— | MS |
| 184 | —(CH$_2$)$_4$NH$_2$ | BO$_2$C$_{10}$H$_{16}$ | 2-OCH$_3$C$_6$H$_4$S— | MS |
| 185 | —(CH$_2$)$_4$NH$_2$ | BO$_2$C$_{10}$H$_{16}$ | 2-OCH$_3$C$_6$H$_4$SO$_2$— | MS |
| 186 | —(CH$_2$)$_4$NH$_2$ | B(OH)$_2$ | 3-OCH$_3$C$_6$H$_4$S— | |
| 187 | —(CH$_2$)$_4$NH$_2$ | B(OH)$_2$ | 3-OCH$_3$C$_6$H$_4$SO$_2$— | |
| 188 | —(CH$_2$)$_4$NH$_2$ | BO$_2$C$_{10}$H$_{16}$ | 4-OCH$_3$C$_6$H$_4$S— | MS |
| 189 | —(CH$_2$)$_4$NH$_2$ | BO$_2$C$_{10}$H$_{16}$ | 4-OCH$_3$C$_6$H$_4$SO$_2$— | MS |
| 190 | —(CH$_2$)$_4$NH$_2$ | BO$_2$C$_{10}$H$_{16}$ | 2-CF$_3$C$_6$H$_4$S— | MS |
| 191 | —(CH$_2$)$_4$NH$_2$ | B(OH)$_2$ | 3-CF$_3$C$_6$H$_4$S— | |
| 192 | —(CH$_2$)$_4$NH$_2$ | B(OH)$_2$ | 4-CF$_3$C$_6$H$_4$S— | |
| 193 | —(CH$_2$)$_4$NH$_2$ | BO$_2$C$_{10}$H$_{16}$ | Ph$_2$PO— | MS |
| 194 | —(CH$_2$)$_4$NH$_2$ | B(OH)$_2$ | PhCH$_2$CH$_2$— | |
| 195 | —(CH$_2$)$_4$NH$_2$ | B(OH)$_2$ | cis-PhCH=CH— | |
| 196 | —(CH$_2$)$_4$NH$_2$ | B(OH)$_2$ | trans-PhCH=CH— | |

TABLE 4

| Ex No. | R¹ | A | R | Data |
|---|---|---|---|---|
| 197 | —(CH$_2$)$_3$SC(=NH)NH$_2$ | BO$_2$C$_{10}$H$_{16}$ | H | MS |
| 198 | —(CH$_2$)$_4$NH$_2$ | BO$_2$C$_{10}$H$_{16}$ | H | MS |
| 199 | —(CH$_2$)$_3$NHC(=NH)NH$_2$ | BO$_2$C$_{10}$H$_{16}$ | NH$_2$CH$_2$— | MS |
| 200 | —(CH$_2$)$_3$NHC(=NH)NH$_2$ | BO$_2$C$_{10}$H$_{16}$ | CBZNH— | MS |
| 201 | —(CH$_2$)$_3$SC(=NH)NH$_2$ | BO$_2$C$_{10}$H$_{16}$ | Ph | MS |
| 202 | —(CH$_2$)$_4$NH$_2$ | BO$_2$C$_{10}$H$_{16}$ | Ph | MS |
| 203 | —(CH$_2$)$_4$NH$_2$ | BO$_2$C$_{10}$H$_{16}$ | PhCH$_2$— | MS |
| 204 | —(CH$_2$)$_3$SC(=NH)NH$_2$ | BO$_2$C$_{10}$H$_{16}$ | CH$_3$(CH$_2$)$_2$CH$_2$— | MS |
| 205 | —(CH$_2$)$_3$SC(=NH)NH$_2$ | BO$_2$C$_{10}$H$_{16}$ | cyclohexyl | MS |
| 206 | —(CH$_2$)$_3$NHC(=NH)NHCH$_3$ | BO$_2$C$_{10}$H$_{16}$ | Ph | MS |
| 207 | —(CH$_2$)$_3$NHC(=NH)NHCH$_3$ | B(OH)$_2$ | Ph | MS |
| 208 | —(CH$_2$)$_3$NHC(=NH)H | BO$_2$C$_{10}$H$_{16}$ | Ph | MS |
| 209 | —(CH$_2$)$_3$NHC(=NH)H | B(OH)$_2$ | Ph | MS |

TABLE 5

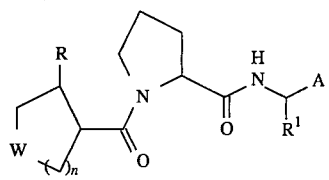

| Ex No. | R¹ | A | n | W | R | Data |
|---|---|---|---|---|---|---|
| 210 | —(CH$_2$)$_4$NH$_2$ | BO$_2$C$_{10}$H$_{16}$ | 1 | NCH$_2$Ph | Ph | MS |
| 211 | —(CH$_2$)$_4$NH$_2$ | BO$_2$C$_{10}$H$_{16}$ | 1 | NBOC | Ph | MS |
| 212 | —(CH$_2$)$_4$NH$_2$ | BO$_2$C$_{10}$H$_{16}$ | 1 | NBOC | 3-CF$_3$C$_6$H$_4$— | MS |
| 213 | —(CH$_2$)$_4$NH$_2$ | BO$_2$C$_{10}$H$_{16}$ | 1 | NH | 3-CF$_3$C$_6$H$_4$— | MS |
| 214 | —(CH$_2$)$_4$NH$_2$ | B(OH)$_2$ | 1 | O | Ph | |
| 215 | —(CH$_2$)$_4$NH$_2$ | B(OH)$_2$ | 1 | S | Ph | |
| 216 | —(CH$_2$)$_4$NH$_2$ | BO$_2$C$_{10}$H$_{16}$ | 2 | CH$_2$ | Ph | MS |
| 217 | —(CH$_2$)$_4$NH$_2$ | B(OH)$_2$ | 2 | CH$_2$ | Ph | MS |
| 218 | —(CH$_2$)$_4$NH$_2$ | B(OH)$_2$ | 1 | CH$_2$ | Ph | |
| 219 | —(CH$_2$)$_4$NH$_2$ | BO$_2$C$_{10}$H$_{16}$ | 1 | NH | Ph | |
| 220 | —(CH$_2$)$_4$NH$_2$ | BO$_2$C$_{10}$H$_{16}$ | 1 | NCBZ | Ph | |
| 221 | —(CH$_2$)$_4$NH$_2$ | BO$_2$C$_{10}$H$_{16}$ | 1 | NAc | Ph | |
| 222 | —(CH$_2$)$_4$NH$_2$ | B(OH)$_2$ | 1 | NH | 3-pyridyl | |

TABLE 6

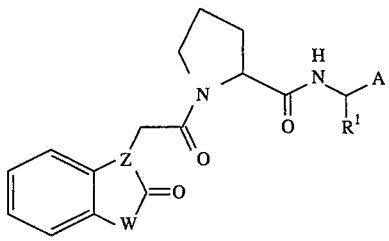

| Ex No. | R¹ | A | Z | W | Data |
|---|---|---|---|---|---|
| 223 | —(CH$_2$)$_3$SC(=NH)NH$_2$ | BO$_2$C$_{10}$H$_{16}$ | N | NCH$_2$CH$_3$ | MS |
| 224 | —(CH$_2$)$_4$NH$_2$ | BO$_2$C$_{10}$H$_{16}$ | N | NCH$_2$CH$_3$ | MS |
| 225 | —(CH$_2$)$_4$NH$_2$ | BO$_2$C$_{10}$H$_{16}$ | N | NH | MS |
| 226 | —(CH$_2$)$_4$NH$_2$ | BO$_2$C$_{10}$H$_{16}$ | N | NCH$_2$(CH$_3$)$_2$ | MS |
| 227 | —(CH$_2$)$_3$SC(=NH)NH$_2$ | B(OH)$_2$ | N | NCH$_2$(CH$_3$)$_2$ | MS |
| 228 | —(CH$_2$)$_3$SC(=NH)NH$_2$ | BO$_2$C$_{10}$H$_{16}$ | N | NCH$_3$ | MS |
| 229 | —(CH$_2$)$_4$NH$_2$ | BO$_2$C$_{10}$H$_{16}$ | CH | NCH$_3$ | MS |
| 230 | —(CH$_2$)$_4$NH$_2$ | BO$_2$C$_{10}$H$_{16}$ | N | O | |
| 231 | —(CH$_2$)$_4$NH$_2$ | BO$_2$C$_{10}$H$_{16}$ | N | NCH$_3$ | MS |
| 232 | —(CH$_2$)$_4$NH$_2$ | B(OH)$_2$ | N | NH | MS |

TABLE 7

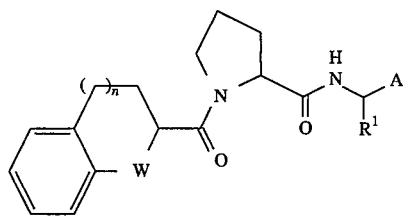

| Ex No. | R¹ | A | n | W | Phys Data |
|---|---|---|---|---|---|
| 233 | —(CH$_2$)$_3$SC(=NH)NH$_2$ | BO$_2$C$_{10}$H$_{16}$ | 1 | CH$_2$ | MS |
| 234 | —(CH$_2$)$_4$NH$_2$ | BO$_2$C$_{10}$H$_{16}$ | 0 | O | MS |
| 235 | —(CH$_2$)$_4$NH$_2$ | BO$_2$C$_{10}$H$_{16}$ | 0 | NH | |
| 236 | —(CH$_2$)$_4$NH$_2$ | BO$_2$C$_{10}$H$_{16}$ | 0 | NCOCH$_3$ | |
| 237 | —(CH$_2$)$_4$NH$_2$ | BO$_2$C$_{10}$H$_{16}$ | 0 | S | |

TABLE 7-continued

| Ex No. | R¹ | A | n | W | Phys Data |
|---|---|---|---|---|---|
| 238 | —(CH$_2$)$_4$NH$_2$ | BO$_2$C$_{10}$H$_{16}$ | 0 | CH$_2$ | |

TABLE 8

| Ex | R¹ | A | R | Phys Data |
|---|---|---|---|---|
| 239 | —(CH$_2$)$_4$NH$_2$ | BO$_2$C$_{10}$H$_{16}$ | -CH$_2$CH$_2$-(2-pyridyl) | MS |
| 240 | —(CH$_2$)$_4$NH$_2$ | BO$_2$C$_{10}$H$_{16}$ | -CH$_2$CH$_2$-(3-pyridyl) | MS |
| 241 | —(CH$_2$)$_3$SC(=NH)NH$_2$ | BO$_2$C$_{10}$H$_{16}$ | -CH$_2$-O-(2-naphthyl) | MS |
| 242 | —(CH$_2$)$_3$SC(=NH)NH$_2$ | BO$_2$C$_{10}$H$_{16}$ | -CH$_2$-O-(1-naphthyl) | MS |
| 243 | —(CH$_2$)$_4$NH$_2$ | BO$_2$C$_{10}$H$_{16}$ | -CH$_2$-O-(pentafluorophenyl) | MS |
| 244 | —(CH$_2$)$_3$NHC(=NH)NH$_2$ | BO$_2$C$_{10}$H$_{16}$ | -CH$_2$-(2-pyridyl) | MS |
| 245 | —(CH$_2$)$_4$NH$_2$ | BO$_2$C$_{10}$H$_{16}$ | -CH$_2$-(1-naphthyl) | MS |

TABLE 8-continued
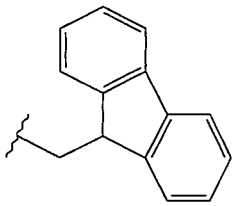
| Ex | R¹ | A | R | Phys Data |
|---|---|---|---|---|
| 246 | —(CH$_2$)$_4$NH$_2$ | BO$_2$C$_{10}$H$_{16}$ | 9-fluorenyl-CH$_2$CH$_2$— | MS |
TABLE 9
| Ex No. | R¹ | A | R | Phys Data |
|---|---|---|---|---|
| 247 | —(CH$_2$)$_3$SC(=NH)NH$_2$ | BO$_2$C$_{10}$H$_{16}$ | 2-naphthyl | MS |
| 248 | —(CH$_2$)$_4$NH$_2$ | BO$_2$C$_{10}$H$_{16}$ | 2-methoxystyryl | MS |
| 249 | —(CH$_2$)$_4$NH$_2$ | BO$_2$C$_{10}$H$_{16}$ | 1-methyl-2-indolyl | MS |
| 250 | —(CH$_2$)$_4$NH$_2$ | BO$_2$C$_{10}$H$_{16}$ | 5-phenyl-3-pyridyl | MS |
| 251 | —(CH$_2$)$_4$NH$_2$ | BO$_2$C$_{10}$H$_{16}$ | 2-phenoxy-3-pyridyl | MS |
| 252 | —(CH$_2$)$_3$SC(=NH)NH$_2$ | BO$_2$C$_{10}$H$_{16}$ | 2-quinolyl | MS |

TABLE 9-continued

| Ex No. | R¹ | A | R | Phys Data |
|---|---|---|---|---|
| 253 | —(CH$_2$)$_4$NH$_2$ | BO$_2$C$_{10}$H$_{16}$ | 4-position of 2-phenylquinoline | MS |

TABLE 10

| Ex No | R¹ | A | R | Phys Data |
|---|---|---|---|---|
| 254 | —(CH$_2$)$_3$SC(=NH)NH$_2$ | BO$_2$C$_{10}$H$_{16}$ | N-(tert-butyl)naphthalene-2-sulfonamidyl | MS |
| 255 | —(CH$_2$)$_4$NH$_2$ | BO$_2$C$_{10}$H$_{16}$ | N-(tert-butyl)naphthalene-2-sulfonamidyl | MS |
| 256 | —(CH$_2$)$_3$SC(=NH)NH$_2$ | BO$_2$C$_{10}$H$_{16}$ | biphenyl-2-carboxamidoethyl | MS |
| 257 | —(CH$_2$)$_4$NH$_2$ | B(OH)$_2$ | dibenzazocinone | MS |

TABLE 10-continued

| Ex No | R¹ | A | R | Phys Data |
|---|---|---|---|---|
| 258 | —(CH₂)₄NH₂ | BO₂C₁₀H₁₆ | | MS |
| 259 | —(CH₂)₃SC(=NH)NH₂ | BO₂C₁₀H₁₆ | | MS |

Utility

The dipeptide boronic acids which are described in the present invention represent a novel class of potent, reversible inhibitors of trypsin-like enzymes. Trypsin-like enzymes are a group of proteases which hydrolyze peptide bonds at basic residues liberating either a C-terminal arginyl or lysyl residue. Among these are enzymes of the blood coagulation and fibrinolytic system required for hemostasis. They are Factors II, X, VII, IX, XII, kallikrein, tissue plasminogen activators, urokinase-like plasminogen activator, and plasmin. Enzymes of the complement system, acrosin (required for fertilization), pancreatic trypsin are also in this group. Elevated levels of proteolysis by these proteases can result in disease states. For example, consumptive coagulopathy, a condition marked by a decrease in the blood levels of enzymes of both the coagulation system, the fibrinolytic system and accompanying protease inhibitors is often fatal. Intervention by a synthetic inhibitor would clearly be valuable. More specifically, proteolysis by thrombin is required for blood clotting. Inhibition of thrombin results in an effective inhibitor of blood clotting. The importance of an effective inhibitor of thrombin is underscored by the observation that conventional anticoagulants such as heparin (and its complex with the protein inhibitor, antithrombin III) are ineffective in blocking arterial thrombosis associated with myocardial infractions and other clotting disorders. However, a low molecular weight thrombin inhibitor, containing a different functionality, was effective in blocking arterial thrombosis [Hanson and Harker (1988) Proc. Natl. Acad. Sci. U.S.A. 85, 3184–3188]. Therefore, we have chosen to demonstrate utility of compounds in the inhibition of thrombin, both as in buffered solutions and in plasma. Specifically, the compounds have utility as drugs for the treatment of diseases arising from elevated thrombin activity such as myocardial infarction, and as reagents used as anticoagulants in the processing of blood to plasma for diagnostic and other commercial purposes.

Compounds of the present invention are expected to be effective in the control of aberrant proteolysis and a number of accompanying disease states such as inflammation, pancretitis, and heritary angioedema.

The effectiveness of compounds of the present invention as inhibitors of the blood coagulation protease thrombin were determined under two different conditions: (1) Measurements in buffered solutions using a synthetic substrate. (2) Measurement in plasma where the rate of blood clotting is determined. For the former, the chromogenic substrate S2238 (Helena Laboratories, Beaumont, Tex.) was used following procedures similar to those described in Kettner et al. 1990. Here hydrolysis resulted in the release of pNA which was monitored spectrophotometricaly by measuring the increase in absorbance at 405 nm. The Michaelis constant, $K_m$, for substrate hydrolysis was determined at 25° C. in 0.10M sodium phosphate buffer, pH 7.5, containing 0.20M NaCl, and 0.5% PEG 8000 using the method of Lineweaver and Burk.

Values of $K_i$ were determined by allowing thrombin (0.19 nM) to react with substrate (0.20 mM) in the presence of inhibitor. Reactions were allowed to go for 30 minutes and the velocities (rate of absorbance change vs time) were measured in the time frame of 25–30 minutes. The following relationship was used to calculate $K_i$ values.

$$\frac{v_o - v_s}{v_s} = \frac{I}{K_i(1 + S/K_m)}$$

where $v_o$ is the velocity of the control in the absence of inhibitor;

$v_s$ is the velocity in the presence of inhibitor;

I is the concentration of inhibitor;

$K_i$ is the dissociation constant of enzyme:inhibitor complex;

S is the concentration of substrate;

$K_m$ is the Michaelis constant.

Inhibition of blood clotting activity of thrombin in plasma was determined in rabbit plasma. Plasma was prepared by diluting blood 1:10 with 3.2% aqueous citric acid and centrifuging. Buffer consisted of 0.10M Tris, pH 7.4, containing 0.9% sodium chloride, and 2.5 mg/mL bovine serum albumin. Bovine thrombin was obtained from Sigma and was diluted to 24 NIH units/mL. Plasma (200 μL) and buffer (50 μL) containing inhibitor were incubated 3 min at 37° C. in a fibrameter. Reactions were initiated by adding thrombin (50 μL) and clotting times measured. Controls were run under identical conditions except in the absence of inhibitor. The final concentration of thrombin was 4 NIH units/mL. The effectiveness of compounds in prolonging clotting times is reported as $IC_{50}$ (level of inhibitor required to prolong clotting to the time observed for 2 NIH units/mL thrombin in the absence of inhibitor). Using the methodology described above, representative compounds of this invention were evaluated and found to exhibit a $K_i$ of less than 1 mM, thereby confirming the utility of the compounds of the invention as effective thrombin inhibitors.

The ability of the compounds to inhibit coagulation was assayed in normal rabbit plasma which was prepared by diluting blood 1:10 with 3.2% aqueous citric acid followed by centrifugation. Bovine thrombin was obtained from Sigma and diluted to 24 NIH units/mL. Plasma (0.2 mL) and buffer (0.05 mL, 0.10M Tris[hydroxymethyl]-aminomethane hydrochloride, pH 7.4, 0.9% (w/v) sodium chloride, and 2.5 mg/mL bovine serum albumin) containing inhibitor were incubated 3 min at 37° C. in a fibrameter. Reactions were initiated by adding thrombin (0.05 mL) to achieve a final concentration of 4 NIH units/mL. The effectiveness of compounds as anticoagulants is reported as the level of inhibitor required to prolong clotting to that observed for 2 NIH units/mL thrombin in the absence of inhibitor. In this assay then, better inhibitors require lower concentrations to delay clot formation. Representative compounds of this invention were evaluated and found to be active.

Since the compounds of formula (I) have anti-thrombogenic properties, they may be employed when an anti-thrombogenic agent is indicated, such as for the control of the coagulation of the fibrinolysis system in mammals or they may be added to blood for the purpose of preventing coagulation of the blood due to contact with blood collecting or distribution containers, tubing or apparatus.

Generally, these compounds may be administered orally, parenterally or intravenously to a host to obtain an anti-thrombogenic effect. The dosage of the active compound depends on the mammalian species, body weight, age, and mode of administration as determined by one skilled in the art. In the case of large mammals such as humans, the compounds may be administered alone or in combination with pharmaceutical carriers or diluents at a dose of from 0.02 to 15 mg/kg to obtain the anti-thrombogenic effect, and may be given as a single dose or in divided doses or as a sustained release formulation.

Pharmaceutical carriers or diluents are well known and include sugars, starches and water, which may be used to make tablets, capsules, injectable solutions or the like which can serve as suitable dosage forms for administration of the compounds of this invention. *Remington's Pharmaceutical Sciences*, A. Osol, is a standard reference text which discloses suitable pharmaceutical carriers and dosage forms. The disclosure of this text is hereby incorporated by reference for a more complete teaching of suitable dosage forms for administration of the compounds of this invention.

What is claimed is:

1. A compound of formula (I)

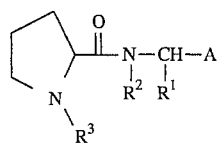

or a pharmaceutically acceptale salt wherein:

$R^1$ is
  a) —($C_1$–$C_{12}$ alkyl)—X, or b) 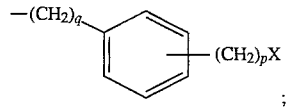

X is
  a) halogen
  b) —CN,
  c) —$NO_2$,
  d) —$CF_3$,
  e) —$NH_2$
  f) —NHC(=NH)H,
  g) —NHC(=NH)NHOH,
  h) —NHC(=NH)NHCN,
  i) —NHC(=NH)$NHR^2$,
  j) —NHC(=NH)NHC(=O)$R^2$,
  k) —C(=NH)$NHR^2$,
  l) —C(=NH)NHC(=O)$R^2$,
  m) —C(=O)$NHR^2$,
  n) —$CO_2R^2$,
  o) —$OR^2$,
  p) —$OCF_3$,
  q) —$SR^2$, or
  r) —SC(=NH)$NHR^2$;

$R^2$ is
  a) hydrogen,
  b) $C_1$–$C_4$ alkyl,
  c) aryl,
  d) —($C_1$–$C_4$ alkyl)-aryl;

$R^3$ is
  a) —C(=O)$CR^6R^7$-aryl,
  b) —C(=O)—($C_2$–$C_5$ alkenyl)-aryl,
  c) —C(=O)$CR^6R^7(CH_2)_r$—W—$(CR^6R^7)_r$-aryl,
  d) —C(=O)$CR^6R^7(CH_2)_r CR^8R^9$-aryl,
  e) —C(=O)$CR^6R^7(CH_2)_r CR^8R^9$-heteroaryl,,
  f) —C(=O)$CR^6R^7(CH_2)_r CR^8R^9$-heterocycle,
  g) —C(=O)-aryl,,
  h) —C(=O)-heteroaryl,
  i) —C(=O)-heterocycle,
  j) —C(=O)O$(CH_2)_r$-adamantyl,
  k) —C(=O)$(CH_2)_r$—($C_5$–$C_7$ cycloalkyl),
  l) —C(=O)$(CH_2)_r$—W—($C_5$–$C_7$ cycloalkyl), m) 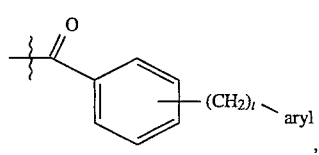

wherein aryl is limited to phenyl, n) 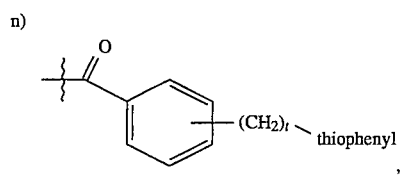
o) 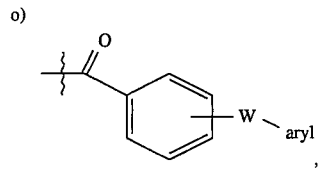
wherein aryl is limited to phenyl,
p) 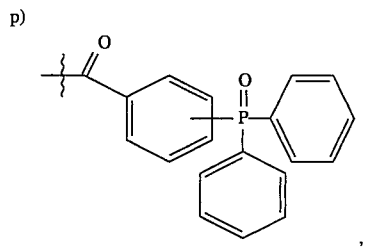
q) 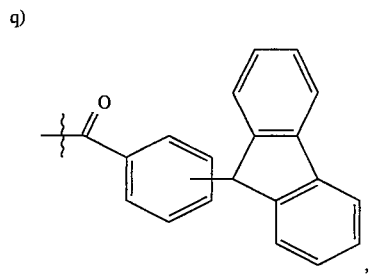
r) 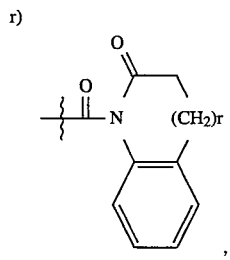
s) 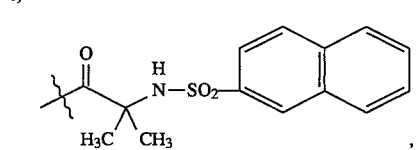
t) 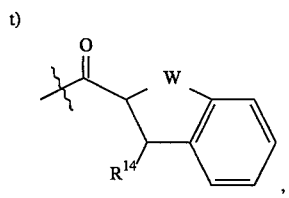
u) 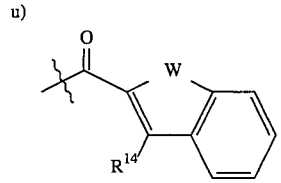
v) 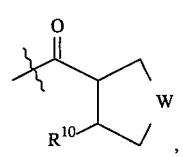
w) 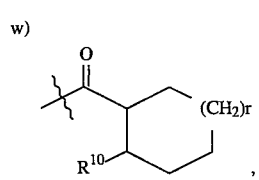
x) 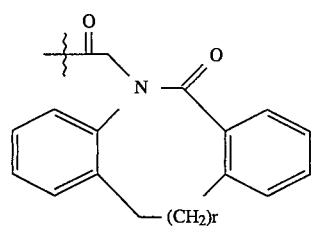
y) 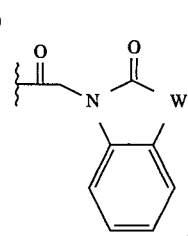
z) 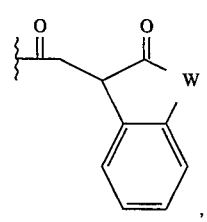
aa) 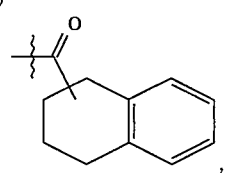

bb) 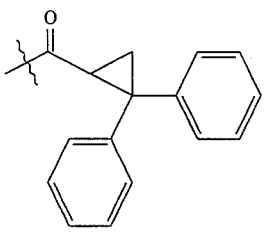

cc) 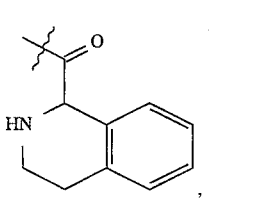

dd) 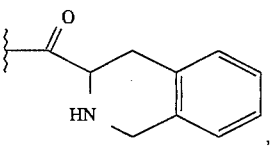

ee) 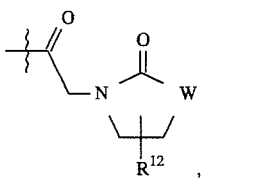

ff) 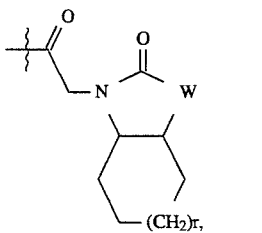

or gg) 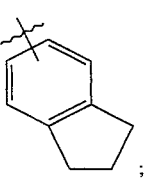

$R^4$ and $R^5$ are independently selected at each occurrence from the group consisting of:
a) hydrogen,
b) $C_1$–$C_4$ alkyl,
c) —($C_1$–$C_4$ alkyl)-aryl, or
d) —$C_5$–$C_7$ cycloalkyl;

$R^6$, $R^7$, $R^8$ and $R^9$ are independently selected at each occurrence from the group consisting of:
a) hydrogen,
b) $C_1$–$C_4$ alkyl,
c) $C_1$–$C_4$ alkoxy,
d) aryl,
e) —($C_1$–$C_4$ alkyl)-aryl,
f) —O—aryl, or
g) —$(CH_2)_p$—$CO_2R^4$;

$R^{10}$ is phenyl, where phenyl is optionally substituted with one to three substituents selected from the group consisting of: halogen, $C_1$–$C_4$ alkyl, $C_1$–$C_4$ alkoxy, methylenedioxy, —$NO_2$, —$CF_3$, —$S(O)_t$—(C1-C4-alkyl), —OH, —$NH_2$, —NH($C_1$–$C_4$ alkyl), —N($C_1$–$C_4$ alkyl)$_2$, —NHC(=O)$R^4$, NHCO$_2R^4$, —$(CH_2)_p$—CO$_2R^4$;

$R^{12}$ is:
a) hydrogen,
b) $C_1$–$C_4$ alkyl,
c) aryl,
c) —($C_1$–$C_4$ alkyl)-aryl, or
d) $C_5$–$C_7$ cycloalkyl;

A is
a) —$BY^1Y^2$,
b) —C(=O)CF$_3$,
c) —PO$_3$H$_2$, or
d) —CO$_2$H;

W is
a) —O—,
b) —S(O)$_r$—,
c) —NR$^4$—,
d) —NC(=O)R$^4$—, or
e) —NCO$_2R^4$—;

$Y^1$ and $Y^2$ are
a) —OH,
b) —F,
c) —NR$^4R^5$,
d) $C_1$–$C_8$ alkoxy, or when taken together $Y^1$ and $Y^2$ form a
e) cyclic boron ester where said chain or ring contains from 2 to 20 carbon atoms and, optionally, 1–3 heteroatoms which can be N, S, or O,
f) cyclic boron amide where said chain or ring contains from 2 to 20 carbon atoms and, optionally, 1–3 heteroatoms which can be N, S, or O,
g) cyclic boron amide-ester where said chain or ring contains from 2 to 20 carbon atoms and, optionally, 1–3 heteroatoms which can be N, S, or O;

n is independently selected at each occurrence from 0 or 1;

p is independently selected at each occurrence from 0 to 3;

q is independently selected at each occurrence from 0 to 4;

r is independently selected at each occurrence from 0 to 2;

t is independently selected at each occurrence from 1 to 3.

2. A compound of claim 1 wherein:

$R^1$ is
a) —(CH$_2$)$_4$NHR$^2$,
b) —(CH$_2$)$_3$NHC(=NH)NHR$^2$,
c) —(CH$_2$)$_3$NHC(=NH)H,
d) —(CH$_2$)$_3$SC(=NH)NHR$^2$;

$R^2$ is hydrogen or $C_1$–$C_4$ alkyl;

$R^3$ is
a) —COCR$^6R^7$-aryl,
b) —COCR$^6R^7$(CH$_2$)$_r$—W—(CR$^6R^7$)$_r$-aryl,
c) —COCR$^6R^7$(CH$_2$)$_r$CR$^8R^9$-aryl,
d) —COCR$^6R^7$(CH$_2$)$_r$CR$^8R^9$-heteroaryl, e)

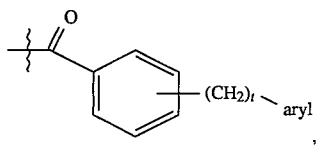

wherein aryl is limited to phenyl, f)

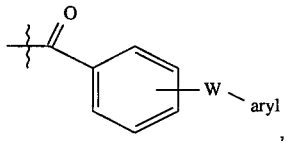

wherein aryl is limited to phenyl, g)

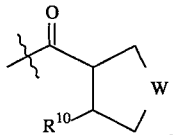

or h)

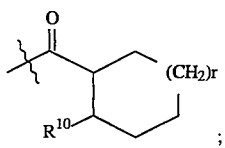

$R^4$ is independently selected at each occurrence from the group consisting of:
a) hydrogen,
b) $C_1$–$C_4$ alkyl,
c) —($C_1$–$C_4$ alkyl)-aryl;

$R^6$, $R^7$, $R^8$, and $R^9$ are independently selected at each occurrence from the group consisting of:
a) hydrogen, or
b) $C_1$–$C_4$ alkyl;

$R^{10}$ is phenyl, where phenyl is optionally substituted with one to three substituents selected from the group consisting of:
halogen, $C_1$–$C_4$ alkyl, $C_1$–$C_4$ alkoxy, —$CF_3$;

A is
a) —$BY^1Y^2$;

W is
a) —O—,
b) —S(O)$_r$—,
c) —$NR^4$—,
d) —NC(=O)$R^4$—, or
e) —$NCO_2R^4$—;

$Y^1$ and $Y^2$ are
a) —OH,
b) $C_1$–$C_8$ alkoxy, or when taken together $Y^1$ and $Y^2$ form a
c) cyclic boron ester where said chain or ring contains from 2 to 20 carbon atoms and, optionally, 1–3 heteroatoms which can be N, S, or O;

r is independently selected at each occurrence from 0 to 2; and t is 1.

3. A compound of claim 2 wherein:

$R^1$ is
a) —($CH_2$)$_4$$NH_2$,
b) —($CH_2$)$_3$NHC(NH)$NH_2$,
c) —($CH_2$)$_3$NHC(NH)H,
d) —($CH_2$)$_3$SC(NH)$NH_2$
e) —($CH_2$)$_3$NHC(NH)$NHCH_3$;

$R^3$ is
a) —$COCR^6R^7(CH_2)_r$—W—($CR^6R^7$)$_r$-aryl,
b) —$COCR^6R^7(CH_2)_r CR^8R^9$-aryl, c)

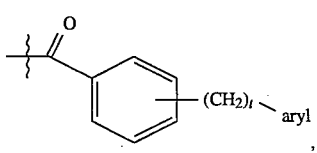

d)

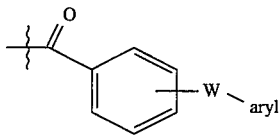

e)

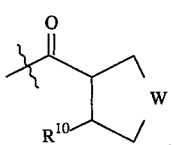

or f)

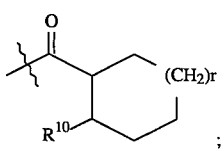

$R^4$ is independently selected at each occurrence from the group consisting of:
a) hydrogen,
b) $C_1$–$C_4$ alkyl,
c) —($C_1$–$C_4$ alkyl)-aryl;

$R^6$, $R^7$, $R^8$, and $R^9$ are independently at each occurrence from the group consisting of:
a) hydrogen, or
b) $C_1$–$C_4$ alkyl;

$R^{10}$ is phenyl, where phenyl is optionally substituted with one to three substituents selected from the group consisting of: halogen, $C_1$–$C_4$ alkyl, $C_1$–$C_4$ alkoxy, methylenedioxy, —$NO_2$, —$CF_3$, —S(O)$_r$-($C_1$–$C_4$ alkyl), —OH, —$NH_2$, —NH($C_1$–$C_4$ alkyl), —N($C_1$–$C_4$ alkyl)$_2$, —NHC(=O)$R^4$, $NHCO_2R^4$ —($CH_2$)$_p$—$CO_2R^4$;

A is
a) —$BY^1Y^2$;

W is
a) —O—,
b) —S(O)$_r$—, c) —NR$^4$—,
d) —NC(=O)R$^4$—, or
e) —NCO$_2$R$^4$—;

Y$^1$ and Y$^2$ are
a) —OH,
b) C$_1$–C$_8$ alkoxy, or when taken together Y$^1$ and Y$^2$ form a
c) cyclic boron ester where said chain or ring contains from 2 to 20 carbon atoms and, optionally, 1–3 heteroatoms which can be N, S, or O;

r is independently selected at each occurrence from 0 to 2; and t is 1.

4. A compound of claim 3 selected from the group consisting of:

(a) PhCH$_2$CH$_2$C(=O)-Pro-NHCH[(CH$_2$)$_3$NHC(=NH)NH$_2$]BO$_2$C$_{10}$H$_{16}$
(b) PhCH$_2$CH$_2$C(=O)-Pro-NHCH[(CH$_2$)$_4$NH$_2$]B(OH)$_2$
(c) PhOCH$_2$C(=O)-Pro-NHCH[(CH$_2$)$_4$NH$_2$]B(OH)$_2$
(d) PhOC(CH$_3$)$_2$C(=O)-Pro-NHCH[(CH$_2$)$_4$NH$_2$]B(OH)$_2$
(e) PhSCH$_2$C(=O)-Pro-NHCH[(CH$_2$)$_4$NH$_2$]B(OH)$_2$
(f) 3-CH$_3$C$_6$H$_4$CH$_2$CH$_2$ C(=O)-Pro-NHCH[(CH$_2$)$_4$NH$_2$]BO$_2$C$_{10}$H16
(g) 2-CF$_3$C$_6$H$_4$CH$_2$CH$_2$ C(=O)-Pro-NHCH[(CH$_2$)$_4$NH$_2$]BO$_2$C$_{10}$H16
(h) (4-CH$_3$O-3-CH$_3$)-C$_6$H$_3$CH$_2$CH$_2$ C(=O)-Pro-NHCH[(CH$_2$)$_4$NH$_2$]BO$_2$C$_{10}$H$_{16}$
(i) 3-[(2-CF$_3$)C$_6$H$_4$CH$_2$]C$_6$H$_4$ C(=O)-Pro-NHCH[(CH$_2$)$_4$NH$_2$]BO$_2$C$_{10}$H$_{16}$
(j) 3-(PhS)C$_6$H$_4$C(=O)-Pro-NHCH[(CH$_2$)$_4$NH$_2$]BO$_2$C$_{10}$H$_{16}$
(k) 3-(PhO)C$_6$H$_4$C(=O)-Pro-NHCH[(CH$_2$)$_4$NH$_2$]BO$_2$C$_{10}$H$_{16}$
(l) trans-[4-(3-CF$_3$C$_6$H$_4$)-Pyrrolidine-3-(C=O)] Pro-NHCH[(CH$_2$)$_4$NH$_2$]BO$_2$C$_{10}$H$_{16}$
(m) [(1R,2R)-2-Phenylcyclohexanecarbonyl] Pro-NHCH[(CH$_2$)$_4$NH$_2$]B(OH)$_2$
(n) 2-(C$_5$H$_4$N)CH$_2$CH$_2$ C(=O)-Pro-NHCH[(CH$_2$)$_4$NH$_2$]BO$_2$C$_{10}$H$_{16}$
(o) 2-(Ph)-C$_6$H$_4$CH$_2$CH$_2$ C(=O)-Pro-NHCH[(CH$_2$)$_4$NH$_2$]BO$_2$C$_{10}$H$_{16}$
(p) 3,4-(Cl)$_2$-C$_6$H$_3$CH$_2$ C(=O)-Pro-NHCH[(CH$_2$)$_3$NHC(=NH)NH$_2$]BO$_2$C$_{10}$H$_{16}$
(q) PhCH$_2$CH$_2$C(=O)-Pro-NHCH[(CH$_2$)$_3$NHC(=NH)H]B(OH)$_2$.

5. A pharmaceutical composition comprising a pharmaceutically suitable carrier and a therapeutically effective amount of a compound of claim 1.

6. A pharmaceutical composition comprising a pharmaceutically suitable carrier and a therapeutically effective amount of a compound of claim 2.

7. A pharmaceutical composition comprising a pharmaceutically suitable carrier and a therapeutically effective amount of a compound of claim 3.

8. A pharmaceutical composition comprising a pharmaceutically suitable carrier and a therapeutically effective amount of a compound of claim 4.

9. A method of treating thrombosis in a warm blooded animal comprising administering to an animal in need of such treatment an effective amount of a compound of claim 1.

10. A method of treating thrombosis in a warm blooded animal comprising administering to an animal in need of such treatment an effective amount of a compound of claim 2.

11. A method of treating thrombosis in a warm blooded animal comprising administering to an animal in need of such treatment an effective amount of a compound of claim 3.

12. A method of treating thrombosis in a warm blooded animal comprising administering to an animal in need of such treatment an effective amount of a compound of claim 4.

* * * * *